(12) United States Patent
Chian et al.

(10) Patent No.: US 8,557,163 B2
(45) Date of Patent: Oct. 15, 2013

(54) MANUFACTURING THREE-DIMENSIONAL SCAFFOLDS USING CRYOGENIC PROTOTYPING

(75) Inventors: Kerm Sin Chian, Holland (SG); Fai Kah Leong, Toa Payoh (SG); Tze Chiun Lim, Sengkang (SG)

(73) Assignee: Nanyang Technological University, Singapore (SG)

( * ) Notice: Subject to any disclaimer, the term of this patent is extended or adjusted under 35 U.S.C. 154(b) by 232 days.

(21) Appl. No.: 12/517,941

(22) PCT Filed: Dec. 5, 2007

(86) PCT No.: PCT/SG2007/000415
§ 371 (c)(1),
(2), (4) Date: Nov. 17, 2009

(87) PCT Pub. No.: WO2008/069761
PCT Pub. Date: Jun. 12, 2008

(65) Prior Publication Data
US 2010/0291176 A1 Nov. 18, 2010

Related U.S. Application Data

(60) Provisional application No. 60/872,795, filed on Dec. 5, 2006.

(51) Int. Cl.
*B28B 3/10* (2006.01)
(52) U.S. Cl.
USPC .......................................................... 264/308
(58) Field of Classification Search
USPC .......................................................... 264/308
See application file for complete search history.

(56) References Cited

U.S. PATENT DOCUMENTS

| | | | |
|---|---|---|---|
| 6,103,255 A | 8/2000 | Levene et al. | |
| 6,231,879 B1 | 5/2001 | Li et al. | |
| 6,899,873 B2 * | 5/2005 | Ma et al. | 424/93.7 |
| 2002/0150753 A1 * | 10/2002 | Ma et al. | 428/357 |
| 2003/0021827 A1 | 1/2003 | Malaviya et al. | |
| 2003/0059460 A1 | 3/2003 | Tabata | |
| 2004/0005297 A1 | 1/2004 | Connelly et al. | |
| 2006/0019362 A1 | 1/2006 | Yu et al. | |
| 2006/0199876 A1 | 9/2006 | Troczynski | |

FOREIGN PATENT DOCUMENTS

| | | |
|---|---|---|
| WO | WO 01/02033 | 1/2001 |
| WO | WO 02/062968 | 8/2002 |
| WO | WO 03/007790 | 1/2003 |
| WO | WO 03/099230 | 12/2003 |
| WO | WO 2004/000915 | 12/2003 |
| WO | WO 2006/099332 | 9/2006 |
| WO | WO 2007/029913 | 3/2007 |

(Continued)

OTHER PUBLICATIONS

U.S. Appl. No. 12/517,701, filed Jun. 4, 2009, Chian, et al.

(Continued)

*Primary Examiner* — Larry Thrower
(74) *Attorney, Agent, or Firm* — Pabst Patent Group LLP

(57) ABSTRACT

The present invention refers to a method of fabricating a three dimensional scaffold suitable for tissue-engineering having a controlled micro- and macroporous structure using cryogenic prototyping. The present invention also refers to scaffolds obtained by the method of the present invention and to their use.

17 Claims, 18 Drawing Sheets

(56) References Cited

FOREIGN PATENT DOCUMENTS

| WO | WO 2007/056418 | 5/2007 |
|---|---|---|
| WO | WO 2008/069759 | 6/2008 |
| WO | WO 2008/069760 | 6/2008 |

OTHER PUBLICATIONS

U.S. Appl. No. 12/517,891, filed Jun. 5, 2009, Chian, et al.
Abstracts of Papers Database accession No. (2007:886977), Aug. 15, 2007.
Albes, et al., "Biophysical properties of the gelatin-resorcin-formaldehyde/glutaraldehyde adhesive.", *The Annals of Thoracic Surgery*, 56(4): 910-915 (1993).
Ang, et al., "Fabrication of 3D chitosan-hydroxyapatite scaffolds using a robotic dispensing system", *Materials Science and Engineering C*, 20(1):35-42 (2002).
Ausubel, et al. "Mutagenesis of Cloned DNA", *Current Protocols in Molecular Biology*, Greene Publishing Associates and Wiley-Interscience, (1987).
Bartold, et al., "Principles and applications of cell delivery systems for periodontal regeneration.", *Periodontology*, 41:123-135 (2006).
Beckstead, et al., "Esophageal epithelial cell interaction with synthetic and natural scaffolds for tissue engineering", *Biomaterials*, 26(31):6217-6228 (2005).
Brannon-Peppas, "Polymers in Controlled Drug Delivery", *Medical Plastics and Biomaterials* (1997).
Brauker, et al., "Neovascularization of synthetic membranes directed by membrane microarchitecture.", *Journal of Biomedical Materials Research*, 29(12):1517-1524 (1995).
Chen, et al., "Development of biodegradable porous scaffolds for tissue engineering", *Materials Science and Engineering*, C17(1-2):63-69 (2001).
Chupa, et al., "Vascular cell responses to polysaccharide materials: in vitro and in vivo evaluations.", *Biomaterials*, 21(22):2315-2322 (2000).
Clark, et al., "Tissue Engineering for Cutaneous wounds", *Journal of Investigative Dermatology*, 127(5):1018-1029 (2007).
Dalton, et al., "Biophysical properties of the gelatin-resorcin-formaldehyde/glutaraldehyde adhesive.", *Biomacromolecules*, 7(3):686-690 (2006).
Demir, et al., "Electrospinning of polyurethane", *Polymer*, 43:3303-3309 (2002).
Deng, et al., "Poly(L-lactic acid)/hydroxyapatite hybrid nanofibrous scaffolds prepared by electrospinning", *Journal of Biomaterials Science*, 18(1):177-130 (2007).
Deng, et al., "Study on biodegradable polymer. 3. Synthesis and characterization of poly(DL-lactic acid)-co-poly(ethylene glycol)-co-poly(L-lysine) co-polymer", *European Polymer Journal*, 38(7):1435-1441 (2002).
Deville, et al., "Freezing as a path to build complex composites", *Science*, 311(5760):515-518 (2006).
Duan, et al., "Hybrid nanofibrous membranes of PLGA/chitosan fabricated via an electrospinning array", *Journal of Biomedical Materials Research*, Part A, 83(3): 868-878 (2007).
Dupont-Gillain and Rouxhet, "Modulable nanometer-scale surface architecture using spin-coating on an adsorbed collagen layer.", *Nano Letters*, 1(5):245-251 (2001).
Endres, et al., "Osteogenic induction of human bone marrow-derived mesenchymal progenitor cells in novel synthetic polymer-hydrogel matrices.", *Tissue Engineering*, 9(4):689-702 (2003).
Ferguson, et al., "Scar-free healing: from embryonic mechanisms to adult therapeutic intervention.", *Philos Trans R Soc Lond B Biol Sci.*, 359(1445):839-850 (2004).
Gilbert, et al., "Decellularization of tissues and organs.", *Biomaterials*, 27(19):3675-3683 (2006).
Griffith, "Emerging design principles in biomaterials and scaffolds for tissue engineering.", *Ann. N.Y. Acad. Sci.*, 961:83-95 (2002).
Han and Gouma, "Electrospun bioscaffolds that mimic the topology of extracellular matrix.", *Nanomedicine: Nanotechnology, Biology and Medicine*, 2(1):37-41 (2006).

Harris and Cooper, L.F., "Comparison of bone graft matrices for human mesenchymal stem cell-directed osteogenesis.", *J Biomed Mater Res A.*, 68(4):747-755 (2004).
Hood, et al., "Perioperative Autologous Sequestration III: A new Physiologic Glue with Wound Healing Properties", *Proceedings of the American Academy of cardiovascular perfusion*, 14:126-129 (1993).
Huang, et al., "A review on polymer nanofibers by electrospinning and their applications in nanocomposites", *Composites Science and Technology*, 63(15):2223-2253 (2003).
Huang, et al., "Electrospraying of a nano-hydroxyapatite suspension", *Journal of Materials Sciences*, 39(3):1029-1032 (2004).
Jain, et al., "Engineering vascularized tissue.", *Nature Biotechnology*, 23(7):821-823 (2005).
Jansen, et al., "Surgical mesh as a scaffold for tissue regeneration in the esophagus.", *European Surgical Research*, 36(2):104-111 (2004).
Jeong, et al., "Tissue-engineered vascular grafts composed of marine collagen and PLGA fibers using pulsatile perfusion bioreactors.", *Biomaterials*, 28(6):1115-1122 (2007).
Kaplan, et al., "Electrospinning *Bombyx mori* silk with poly(ethylene oxide).", *Biomacromolecules*, 3(6):1233-1239 (2002).
Kim, et al., "Control of degradation rate and hydrophilicity in electrospun non-woven poly(D,L-lactide) nanofiber scaffolds for biomedical applications.", *Biomaterials*, 24(27):4977-4985 (2003).
Klawitter, et al., "An evaluation of bone growth into porous high density polyethylene.", *J Biomed Mater Res*, 10(2):311-323 (1976).
Lannutti, et al., "Electrospinning for tissue engineering scaffolds", *Materials Science and Engineering C*, 27:504-509 (2007).
Larrondo, et al, "Electrostatic Fiber Spinning from Polymer Melts. III.Electrostatic Deformation of a Pendant Drop of Polymer Melt", *Journal of Polymer Science: Polymer Physics Edition*, 19( ):933-940 (1981).
Lee, et al, "Frost formation on a vertical plate in simultaneously developing flow", *Experimental Thermal and Fluid Science*, 26:939-945 (2002).
Levenberg, et al., "Engineering vascularized skeletal muscle tissue.", *Nature Biotechnology*, 23(7):879-884 (2005).
Lheureux, et al., *Journal of Vascular Surgery*, 17:499-509 (1993).
Li and Xia, "Electrospinning nanofibres as uniaxially aligned arrays and layer-by-layer stacked films", *Advanced Materials*, 16:1151-1170 (2004).
Li, et al, "Electrospun nanofibrous structure: A novel scaffold for tissue engineering", *J Biomed Mater Res*, 60(4):613-621 (2002).
Li, et al., "Effects of filtration seeding on cell density, spatial distribution, and proliferation in nonwoven fibrous matrices.", *Biotechnology Progress*, 17(5):935-944 (2001).
Li, et al., "Low-molecular-weight peptides derived from extracellular matrix as chemoattractants for primary endothelial cells.", *Endothelium*, 11(3-4):199-206 (2004).
Libbrecht, "The physics of snow crystals", *Reports on Progress in Physics*, 68(4):855-895 (2005).
Lindberg and Badylak, "Porcine small intestinal submucosa (SIS): a bioscaffold supporting in vitro primary human epidermal cell differentiation and synthesis of basement membrane proteins.", *Burns*, 27(3):254-266 (2001).
Liu, et al., "Experimental study on the ice pattern fabrication for the investment casting by rapid freeze prototyping (RFP)", *Computers in Industry*, 48(3):181-197 (2002).
Liu, et al., "Ordered porous ZnO thin films formed by dip-coating method using PS templates", *Journal of Sol-Gel Science and Technology*, 40(1):25-30 (2006).
Liu, et al., "Porous morphology, porosity, mechanical properties of poly(alpha-hydroxy acid)-tricalcium phosphate composite scaffolds fabricated by low-temperature deposition", *Journal of Biomedical Material Research Part A*, 82(3):618-629 (2007).
Ma, "Scaffolds for tissue fabrication.", *Materials Today*, 7(5):30-40 (2004).
MacNeil, "Progress and opportunities for tissue-engineered skin", *Nature*, 445(7130):874-880 (2007).
Mao, et al., "Structure and properties of bilayer chitosan-gelatin scaffolds", *Biomaterials*, 24(6):1067-1074 (2003).

(56) References Cited

OTHER PUBLICATIONS

Marshall, et al., *Abstracts of Papers of the American Chemical Society*, 228:U386-U386 (2004).

Megelski, et al., "Micro- and Nanostructured Surface Morphology on Electrospun Polymer Fibers", *Macromolecules*, 35(22):8456-8466 (2002).

Meyer, et al., "Extracellular matrix proteins in the porcine pancreas: a structural analysis for directed pancreatic islet isolation.", *Transplant Proc.*, 30(2):354 (1998).

Mo, et al., "Electrospun P(LLA-CL) nanofiber: a biomimetic extracellular matrix for smooth muscle cell and endothelial cell proliferation", *Biomaterials*, 25(10):1883-1890 (2004).

Moran, et al., "Characterization of polylactic acid-polyglycolic acid composites for cartilage tissue engineering.", *Tissue Engineering*, 9(1):63-70 (2003).

Oh, et al., "In vitro and in vivo characteristics of PCL scaffolds with pore size gradient fabricated by a centrifugation method", *Biomaterials*, 28(9):1664-1671 (2007).

Pham, et al., "Electrospinning of polymeric nanofibers for tissue engineering applications: a review.", *Tissue Engineering*, 12(5):1197-1211 (2006).

Robinson, et al., "Myocardial tissue replacement with extracellular matrix scaffolds", *J Am Coll Cardiol*, 41(6):514 (2003).

Sambrook, et al., *Molecular Cloning: A Laboratory Manual*, Cold Spring Harbour Lab Publ., (1989).

Schantz, et al., *A Manual for Primary Human Cell Culture*, World Scientific Publishing Company, (2004).

Schenke-Layland, et al., "Impact of decellularization of xenogeneic tissue on extracellular matrix integrity for tissue engineering of heart valves.", *J Struct Biol*, 143(3):201-208 (2003).

Schindler, et al., "A synthetic nanofibrillar matrix promotes in vivo-like organization and morphogenesis for cells in culture.", *Biomaterials*, 26(28):5624-5631 (2005).

Smith and Ma, "Nano-fibrous scaffolds for tissue engineering", *Colloids and Surfaces B: Biointerfaces*, 39:125-131 (2004).

Smith and Stolle, "Nonisothermal two-dimensional film casting of a viscous polymer", *Polym. Eng. Sci.*, 40(8):1870-1877 (2000).

Stankus, et al., "Microintegrating smooth muscle cells into a biodegradable, elastomeric fiber matrix.", *Biomaterials*, 27(5):735-744 (2006).

Subbiah, et al., "Electrospinning of nanofibers", *Journal of Applied Polymer Science*, 96(2):557-569 (2005).

Sun, et al., "Frost formation on a vertical plate in simultaneously developing flow", *Applied Physics Letters*, 86(11):113504 (2005).

Sunderkötter, et al., "Macrophage-derived angiogenesis factors.", *Pharmacology & Therapeutics*, 51(2):195-216 (1991).

Sutherland, et al., "Regeneration of bladder urothelium, smooth muscle, blood vessels and nerves into an acellular tissue matrix.", *J Urol*, 156(2 pt 2):571-577 (1996).

Thorn, et al., "Autologous fibrin glue with growth factors in reconstructive maxillofacial surgery.", *J Oral Maxillofac. Surg*, 33(1):95-100 (2004).

Valentin, et al., "Extracellular matrix bioscaffolds for orthopaedic applications. A comparative histologic study.", *J Bone Joint Surg Am*, 88(12):2673-2686 (2006).

Wu, et al., "Preparation and assessment of glutaraldehyde-crosslinked collagen-chitosan hydrogels for adipose tissue engineering.", *Journal of Biomedical Materials Research Part A*, 81A(1):59-65 (2007).

Yan, et al., "Layered manufacturing of tissue engineering scaffolds via multi-nozzle deposition", *Material Letters*, 57(18):2623-2628 (2003).

Yang, "The design of scaffolds for use in tissue engineering. Part I. Traditional factors.", *Tissue Engineering*, 7(6):679-689 (2001).

Yang, et al., "The design of scaffolds for use in tissue engineering. Part II. Rapid prototyping techniques.", *Tissue Engineering*, 8(1):1-11 (2002).

Zeltinger, et al., "Effect of pore size and void fraction on cellular adhesion, proliferation, and matrix deposition.", *Tissue Engineering*, 7(5):557-572 (2001).

Zhang, et al., "Aligned porous structures by directional freezing", *Adv. Mater.*, 19:1529-1533 (2007).

Zhang, et al., "Poly($\alpha$-hydroxyl acids)/hydroxyapatite porous composites for bone-tissue engineering.", *J Biomed Mater Res*, 44:446-455 (1999).

Zhou, et al., "The thermal effects on electrospinning of polylactic acid melts", *Polymer*, 47(21):7497-7505 (2006).

\* cited by examiner non-shifted        shifted shifted in any direction

MANUFACTURING THREE-DIMENSIONAL SCAFFOLDS USING CRYOGENIC PROTOTYPING

CROSS-REFERENCE TO RELATED APPLICATIONS

This application is a filing under 35 U.S.C. 371 of PCT/SG2007/000415 filed in the Singapore Receiving Office of the Patent Cooperation Treaty on Dec. 5, 2007, which claims the benefit of priority of U.S. provisional application No. 60/872,795, filed Dec. 5, 2006, the contents of each being hereby incorporated by reference in its entirety for all purposes.

FIELD OF THE INVENTION

The present invention refers to a method of fabricating a three dimensional scaffold suitable for tissue-engineering having a controlled micro- and macroporous structure using cryogenic prototyping. The present invention also refers to scaffolds obtained by the method of the present invention and to their use.

BACKGROUND OF THE INVENTION

Scaffolds are artificial structures capable of supporting a three-dimensional tissue formation. Scaffolds are supposed to resemble the connective tissue in an extracellular matrix. Thus, scaffolds allow for cell attachment, migration and growing of cells and synthesis of extracellular matrix components and biological molecules specific to the tissue targeted for replacement. To achieve those objects, a scaffold ideally provides a high porosity and proper pore size, a high surface area, biodegradability, proper degradation rate to match the rate of neotissue formation and it should provide a sufficient mechanical integrity to maintain the predesigned tissue structure. A scaffold should also be nontoxic to the cells (i.e. biocompatible) and should positively interact with cells including enhanced cell adhesion, growth, migration, and differentiated function (Ma, P. X., May 2004, Materials Today, p. 30-40).

The control of pore size is an important aspect for tissue engineering scaffolds. It has been shown in numerous studies that different pore sizes have different interactions for different cell types. One example to illustrate is a study done on the response of three cell types (canine dermal fibroblasts, vascular smooth muscle cells, and microvascular epithelial cells) to porous poly(L-lactic acid) scaffolds with four pore size distribution (<38, 38-63, 63-106, and 106-150 µm) (Zeltinger, J., Sherwood, J. K. et al., 2001, Tissue Engineering, vol. 7, no. 5, p. 557-572). Vascular smooth muscle cells displayed higher cell proliferation and extracellular matrix synthesis for larger pore sizes (106-150 µm). While, endothelial cells show a preference for pores less than 38 µm, forming a connected multicellular lining.

In addition, it is known that a specific range of pore sizes is required for different tissue engineering applications. For effective cell growth and tissue regeneration, a pore size range of 380 to 405 µm is required for chondrocytes and osteoblasts, 186 to 200 µm for fibroblasts and 290 to 310 µm for new bone formation. Therefore, it is important for scaffold fabricating techniques to be able to create three-dimensional (3-D) scaffolds of a range of controlled macro and micro-porosities to allow customization for different tissue engineering applications.

The creation of such scaffolds, with complex geometry for tissue regeneration purposes, has been one of the major challenges in tissue engineering. Fabrication techniques must provide three levels of control: (a) macroscopic and composition (mm to cm), (b) size orientation and surface chemistry of pores and channels for tissue ingrowth (hundreds of µm) and (c) locally surface texture and porosity (10 µm) (Griffith, L. G., 2002, Ann. N.Y. Acad. Sci., vol. 961, p. 83-95).

Many scaffolds used as implants and for tissue engineering purposes are fabricated by conventional methods (i.e., particulate leaching, fiber bonding, solvent casting, membrane lamination, melt molding, gas forming and phase separation). However, these methods are limited in that they typically generate scaffolds with simple macro-architectures and homogeneous microstructures, i.e. the micro- and macro pore size, geometry and connectivity in different layers of the scaffold cannot be well controlled (Yang, S., Leong, K.-F. et al., 2002, Tissue Engineering, vol. 8, no. 1, p. 1-11). However, since scaffolds are supposed to replace, for example, structural tissue like bone, cartilage, skin and esophagus, which do not normally have a complete homogeneous structure but are made of different layers which are structured depending on their special function and cell species which are growing in these different layers, artificial scaffolds also need to provide such a complex structure and not only a structure which provides only one specific pore size or one specific texture.

Rapid prototyping (RP) is a recent technology based on the use of computer control in manufacturing. Rapid prototyping takes virtual three dimensional designs from computer aided design (CAD), transforms them into thin, virtual, horizontal two-dimensional cross-sections and then creates each cross-section in physical space, one layer after the next until the three-dimensional model is finished. These two-dimensional layers can be made and bonded to previous layers one by one sequentially (Liu, Q., Sui, G., Leu, M. C., 2002, Computers in Industry, vol. 48, p. 181-197).

However, commonly used RP methods such as Fused Deposition Modeling (FDM) and Selective Laser Sintering (SLS) require elevated processing temperatures and this limits their ability to process temperature-sensitive polymers and bioactive components.

Ang, T. H., Sultana, F. S. A. et al. (2002, Materials Science and Engineering C, vol. 20, p. 35-42) describe a rapid prototyping method comprising bioplotting. This method is carried out at room temperature, where a solution is dispensed into a medium and subsequent reaction causes the solution to solidify and retain its dispensed path. The hydrogel scaffold obtained was subsequently frozen and freeze dried. Macropores of 400 to 1000 µm can be created with this technique by spacing the dispensed solution path. However, surface microporosity was not observed at all, as the coagulation process usually forms a skin at the surface.

Yan, Y., Xiong, Z., et al. (2003, Material Letters, vol. 57, p. 2623-2628) describe a system termed multi-nozzle deposition manufacturing (MDM) which is used to fabricate tissue engineered scaffolds for bone. Tricalcium phosphate (TCP) particles have been added to PLLA in dioxane and dispensed in a low temperature environment of under 0° C. The scaffold was subsequently freeze dried to obtain an interconnected porous structure at room temperature. The micropore obtained is about 400 µm while the micropores are about 5 µm. The scaffolds obtained comprise micropores of random orientation.

U.S. Pat. No. 6,899,873 B2 describes the manufacture of scaffolds by casting polymer solution into molds which are then frozen and freeze dried. Freezing temperatures and solvents can be used to control porosity and diameter of micropores. The ability to orientate the direction of the micropores is also demonstrated by creating a temperature gradient during freezing. PLLA scaffolds of different porosities (pore sizes from 50 to 100 µm) can be obtained. However, for this method it will be difficult to create three dimensional scaffolds with customized macro features. This method does also not allow fabrication of scaffolds having different micropore orientations and sizes within a scaffold.

Since there is a demand for scaffolds having a complex micro- and macrostructure further methods are required to provide such scaffolds.

SUMMARY OF THE INVENTION

In a first aspect the present invention is directed to a method of fabricating a three dimensional scaffold suitable for tissue-engineering having a controlled macroporous and macroporous structure using cryogenic prototyping comprising:
  a) dispensing a first polymer solution in one direction into a reaction chamber to form a ffirst lane;
    wherein the first polymer solution comprises a first polymer and a first solvent;
    wherein the reaction chamber has a first temperature which is at or below the freezing point of the first solvent;
  b) dispensing a second polymer solution into the reaction chamber to form a second lane;
    wherein the second polymer solution comprises a second polymer and a second solvent;
    wherein the second polymer solution is dispensed such that the second lane is arranged next to the first lane in the same orientation as the first lane and being in contact with the first lane on one side;
    wherein the reaction chamber has a second temperature, wherein the second temperature is the same or different from the first temperature as long as it is at or below the freezing point of the second solvent; and
  c) dispensing further polymer solutions into the reaction chamber by repeating steps a) and b) to form further lanes in a first plane;
  d) repeating steps a) to c) to form further lanes in a next plane,
    wherein at least some of the lanes in the next plane are in contact with the lanes of the first plane;
  e) repeating step d) to form a three-dimensional scaffold comprising different planes of lanes formed by the polymer solutions;
    wherein in any of steps c) to d) the polymer solutions are dispensed such that macropores of the controlled macroporous structure are created;
  f) removing the solvents from the three-dimensional scaffold so obtained.

In another aspect, the present invention is directed to a method of fabricating a three dimensional scaffold suitable for tissue-engineering having a controlled micro- and macroporous structure using cryogenic prototyping comprising:
  a) dispensing multiple threads or drops of a first polymer solution into a reaction chamber to form a first plane;
    wherein the first polymer solution comprises a first polymer and a first solvent;
    wherein the reaction chamber has a first temperature which is at or below the freezing point of the first solvent;
  b) dispensing multiple threads or drops of a second polymer solution into the reaction chamber to faun a second plane;
    wherein the second polymer solution comprises a second polymer and a second solvent;
    wherein the second threads or drops are in contact with the deposited threads or drops of the first plane but are laterally shifted in any direction with respect to the threads or drops forming the first plane when they are dispensed into the reaction chamber;
    wherein the reaction chamber has a second temperature, wherein the second temperature is the same or different from the first temperature as long as it is at or below the freezing point of the second solvent;
  c) dispensing multiple threads or drops of a third polymer solution into the reaction chamber to form a third plane;
    wherein the third polymer solution comprises a third polymer and a third solvent;
    wherein the third threads or drops are in contact with the deposited threads or drops of the second plane but are laterally shifted in any direction with respect to the deposited threads or drops of the first plane when they are dispensed into the reaction chamber in the same direction as the first plane;
    wherein the reaction chamber has a third temperature, wherein the third temperature is the same or different from the first and/or second temperature as long as it is at or below the freezing point of the third solvent;
  d) dispensing further threads or drops of polymer solutions into the reaction chamber to form further planes by repeating steps a) to c) to obtain the three-dimensional scaffold;
    wherein the macroporous structure of the scaffold is defined by controlling within one plane the distance of at least some of the multiple threads or drops to each other;
    wherein the microporous structure of the scaffold is defined by controlling the temperature of the reaction chamber when dispensing the polymer solutions into the reaction chamber; and
  e) removing the solvent of the three-dimensional scaffold.

In another aspect, the present invention is directed to the use of a method according to the present invention for the manufacture of scaffolds for tissue engineering.

In still another aspect, the present invention is directed to a scaffold obtained by a method according to the present invention.

BRIEF DESCRIPTION OF THE DRAWINGS

The invention will be better understood with reference to the detailed description when considered in conjunction with the non-limiting examples and the accompanying drawings, in which:

In FIG. 7 (left picture) the lanes are placed on top of each other in different planes whereas in FIG. 8 (right picture) the lanes are placed in radial orientation next to each other in the same plane.

FIGS. 14 a and b show a scaffold having a grid pattern as known in the prior art (see for example Yan, Y., Xiong, Z., et al., 2003, supra). FIGS. 14 a and b reflect the structure shown in FIG. 21b.

FIG. 21 shows the layered structure of different scaffolds which have polymer lanes dispensed in different planes in a position to each other which is laterally shifted (FIG. 21 c-h) and scaffolds which have polymer lanes which are dispensed in a position relative to each other which is not laterally shifted (non-shifted) (FIGS. 21 a and b). "x" indicates the direction seen in a three-dimensional space as it is illustrated by the coordinate system in the middle of FIG. 21. FIGS. 21a to e are side views on a scaffold whereas FIGS. 21 f to h are top views of a scaffold. Thus, "laterally shifted" means that one thread or drop of polymer solution is staggered with respect to another thread or drop as illustrated in FIG. 21 c. In other words a thread or drop of polymer solution is displaced to any side and in any direction in another plane. With laterally shifted "in any direction" is meant that the thread or drop can be staggered (overlaps) in any direction with respect to another thread or drop of another plane. The numbering of the polymer threads given in FIG. 21 f also refers to FIG. 21 g and h. FIG. 21 h illustrates the meaning of the phrase "in any direction" when comparing FIG. 21 h with FIG. 21 f or g. In FIGS. 21 f and g the threads of plane 112 is staggered parallel with respect to the threads of plane 111. Polymer thread 113 is lying between 111 and 112. The scheme in FIG. 21 d is corresponding to the scheme in FIG. 21 f. With "any direction" it is meant that one thread, e.g. thread 2, can not only be staggered parallel to another thread in another plane, e.g. threads of plane 111, but can also be staggered in any other direction as for example threads of plane 111 and 112 in FIG. 21 b. The structure of FIG. 21 b is reflected in FIG. 14 a and b which shows a simple grid pattern as known in the prior art (see for example Yan, Y., Xiong, Z., et al., 2003, supra).

FIG. 23 shows a three-dimensional drawing of a three-dimensional scaffold with simulated polymer dispensing paths to show how the scaffold is fabricated. The scaffold is fabricated by dispensing polymer in a designed path. The polymer thread dispensed from the needle and frozen will be named lane 101. The spacing in between lanes will be termed gaps 102. In order to create a temperature gradient, the lane 101 should be in contact when dispensed next to each other; therefore the gaps are usually kept at zero. Next, the feature to define is the macropore 103 which has a channel like structure in this figure. This macropores will be used to describe spaces in the scaffold which are incorporated into the computer-aided design (CAD). These macropores can be of any design and during the fabrication process, polymer will not be dispensed in that area. Lastly, pores 104 are defined as structures within the lanes which are formed as a result of phase separation during freezing. As the polymer freezes, solvent crystals are formed and the polymer phase separates. After, e.g., freeze drying to remove the solvent crystals, a scaffold with pores in the polymer lanes will be obtained.

In FIG. 24 (left picture) the lanes are placed on top of each other in different planes whereas in FIG. 24 (right picture) the lanes are placed in radial orientation next to each other in the same plane.

FIG. 28 below show the cross section of the esophagus. The innermost layer 401 is the mucosa which is a thick layer of stratified squamous epithelium. Next is the submucosa 402 which contains the mucous secreting glands and loosely connects the mucosa to the muscle layer. The muscularis externa consists of two planes of muscle of different orientation. The inner layer 403 has muscle fibers arranged circumferentially while in the outer layer 404, the fibers are arranged longitudinally. Hence for designing a scaffold for esophageal tissue engineering, it is important to mimic the structure of the esophagus and provide orientation for smooth muscle cells.

DETAILED DESCRIPTION OF THE INVENTION

For many kind of tissues it is known that isolated cells of these tissues cannot form new functional tissues by themselves. Most primary organ cells are believed to be anchorage-dependent and require specific environments that very often include the presence of a supporting material to act as a template for growth. The success of any cell transplantation therapy therefore relies on the development of suitable substrates for both in vitro and in vivo tissue culture. Currently, these substrates, mainly in form of tissue engineering scaffolds, prove less than ideal for applications because they suffer from a lack of interconnection channels and specific different structure of different scaffold layers that allow cell growth to penetrate such three dimensional matrices (i.e. scaffolds).

The regeneration of specific tissues aided by synthetic materials has been shown to be dependent on the porosity and pore size of the supporting three-dimensional structure of the scaffold. A large surface area favors cell attachment and growth, whereas a large pore volume is required to accommodate and subsequently deliver a cell mass sufficient for tissue repair. Highly porous biomaterials are also desirable for the easy diffusion of nutrients to and waste products from the implant and for vascularization which are major requirements for the regeneration of highly metabolic organs. The surface area/volume ratio of porous materials depends on the density and average diameter of the pores. Nevertheless, the diameter of cells in suspension dictates the minimum pore size, which varies from one cell type to another.

Figure 28:
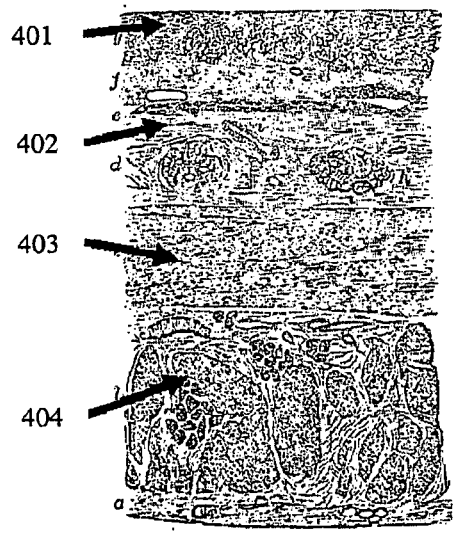
FIG. 28 illustrates the structure of esophagus. In a non-limiting example of the present invention a three-dimensional scaffold has been fabricated to replace parts of esophageal tissue. The esophagus is a tubular organ which extends from the pharynx to the stomach, its main function being to secrete mucus and transport food to the stomach.

Insofar certain tissues depend on more than one cell type, a corresponding scaffold on which those cells are supposed to be seeded needs to provide a micro and macroporous structure suitable for those different cell types. For example, cells of a complex environment, such as the periodontium require the delivery of cells of multiple phenotypes. If one wanted to regenerate both periodontal ligament and alveolar bone, it would be necessary to seed periodontal ligament cells and osteoblasts into a scaffold [Bartold, P. M., Xiao, Y., et al., 2006, Periodontology, vol. 41, p. 123-135]. Another example would be an artificial scaffold as replacement for skin. Skin consists of three different layers, epidermis, dermis and hypodermis. The epidermis contains keratinocytes with melanocytes and Langerhans' cells also present. The dermis contains the hair follicles, sweat glands, sebaceous glands, apocrine glands, lymphatic vessels and blood vessels. Types of cells that are found in the hypodermis are fibroblasts, adipose cells, and macrophages. When trying to create scaffolds for tissue-engineering of esophageal tissue or parts thereof, one would have to mimic a structure as illustrated in FIG. 28.

Thus, scaffolds suitable for the replacement of such complex tissues require a scaffold with a diverse micro and macroporous structure which provides the structural conditions required by the different cell types which can be normally found in this tissue.

However, until today no method exists which would allow manufacture of such complex scaffolds in one passage providing a scaffold with a continuous porous structure with yet variable micro and macroporous structure. For example, the method described by Yan, Y., Xiong, Z. et al. (2003, supra) allows the manufacture of scaffolds with differing macroporous structure but the microporous structure is uniform and can not be varied within one scaffold.

Therefore, the inventors provide a method of fabricating a three dimensional scaffold suitable for tissue-engineering having a controlled micro- and macroporous structure using rapid prototyping comprising in a first example:
  a) dispensing a first polymer solution in one direction into a reaction chamber to form a first lane;
     wherein the first polymer solution comprises a first polymer and a first solvent;
     wherein the reaction chamber has a first temperature which is at or below the freezing point of the first solvent;
  b) dispensing a second polymer solution into the reaction chamber to form a second lane;
     wherein the second polymer solution comprises a second polymer and a second solvent;
     wherein the second polymer solution is dispensed such that the second lane is arranged next to the first lane in the same orientation as the first lane and being in contact with the first lane on one side;
     wherein the reaction chamber has a second temperature, wherein the second temperature is the same or different from the first temperature as long as it is at or below the freezing point of the second solvent; and
  c) dispensing further polymer solutions into the reaction chamber by repeating steps a) and b) to form further lanes in a first plane;
  d) repeating steps a) to c) to form further lanes in a next plane,
     wherein at least some of the lanes in the next plane are in contact with the lanes of the first plane;
  e) repeating step d) to form a three-dimensional scaffold comprising different planes of lanes formed by the polymer solutions;
     wherein in any of steps c) to d) the polymer solutions are dispensed such that macropores of the controlled macroporous structure are created;
  f) removing the solvents from the three-dimensional scaffold so obtained.

Figure 23:
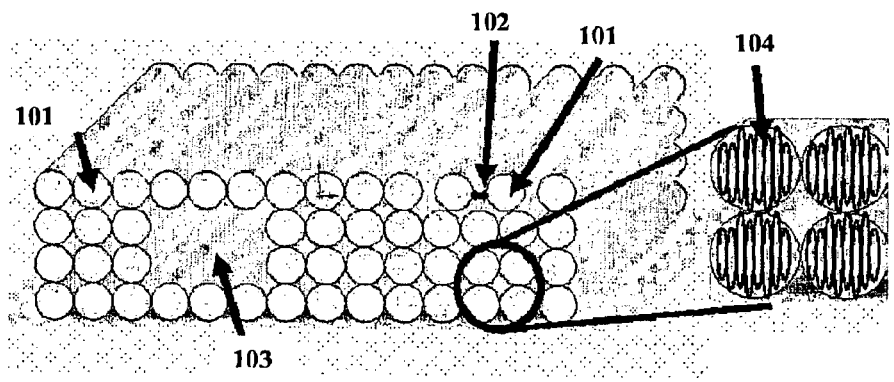
FIG. 23 shows a scheme illustrating the manufacture of a three-dimensional scaffold according to claim 1.
Figure 24:
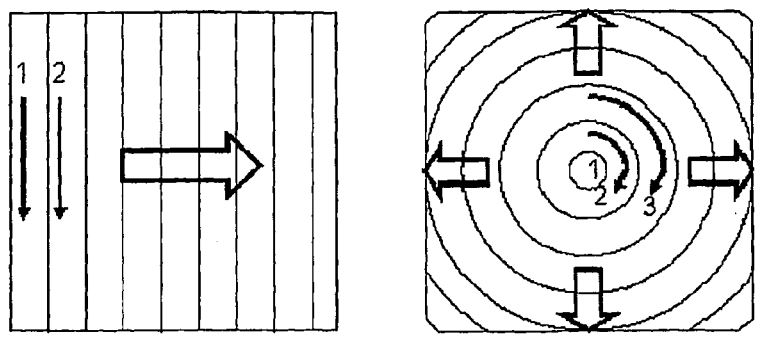
FIG. 24 shows the direction of the temperature gradients which will be created between the previous lane and the newly deposited lane (indicated by an solid arrow). The big non-solid arrows in FIG. 24 also indicate the direction of crystal growth within the different lanes of the embodiments illustrated in FIGS. 7 and 8.
Figure 25:
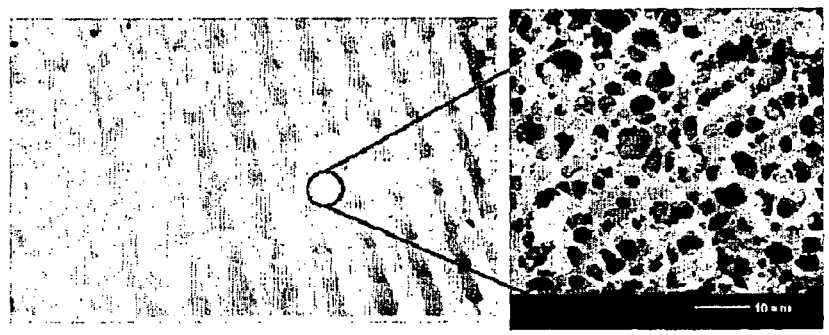
FIGS. 25 and 26 demonstrate the manufacture of scaffolds according to the article of Yan, Y., Xiong, Z., et al. (2003, supra). According to this article the scaffold is manufactured by dispensing polymer threads in a regular grid structure, with one plane with threads in the x axis and the next plane with threads in the y axis. The pores obtained with is dispensing path is random with no fixed orientation, as seen in the SEM picture of FIG. 25. By dispensing in this grid structure, the polymer thread is not in full contact with the lanes of the previous frozen lane. As a result, a temperature gradient cannot be created for the dispensed polymer lane to form oriented pores. In addition, the frozen polymer lanes are fused only through the contact points 2001 (circles) and not throughout the whole scaffold as illustrated in FIG. 26. Pores created for this design will not be fully fused and continuous as at obtained via cryogenic prototyping as seen in FIGS. 4 and 23.
Figure 26:
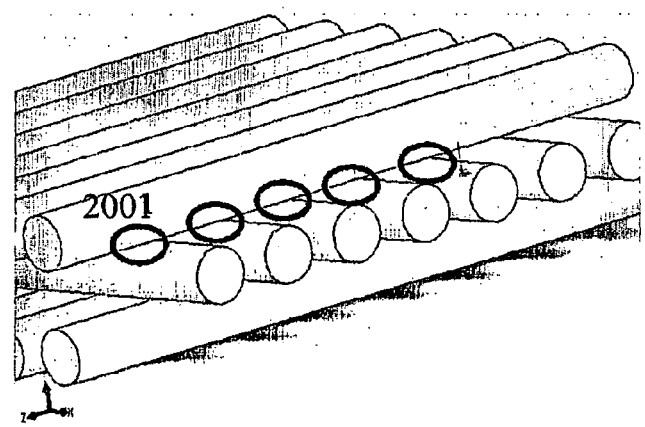

For a scaffold fabricated according to this method, the macroporous structure is thus defined by controlling the temperature of the reaction chamber when dispensing the polymer solution into the reaction chamber. In general, the temperature difference thus created between the polymer dispensed into the reaction chamber and the temperature within the reaction chamber will affect the rate of cooling and thus the pore size which depends on the size of crystals formed from the solvent as illustrated further below. Thus, for the methods of the present invention, the temperature difference is determined by two temperatures, the temperature of the polymer solution and the temperature within the reaction chamber. Both can be controlled to obtain the desired temperature difference. Examples for the assembly of such a scaffold are given, for example, in FIGS. 9, 23 and 29.

In this method it is mentioned that the second polymer solution is dispensed such that the second lane is arranged next to the first lane "in the same orientation" as the first lane and being in contact with the first lane on one side. With the "same orientation" is meant that the second polymer needs to be dispensed in the same layout which does not necessarily mean that it has to follow the same direction to be in the same orientation as the first lane. For example, a first lane is started to be dispensed into the reaction chamber at point A and stops at point B. Now it is possible to dispense the second lane either starting at point A and going towards point B or to start at point B and going towards point A. As long as both lanes are oriented next to each other they are considered to be in the same orientation.

A "plane" refers to a surface in which if any two points are chosen a straight line joining them lies wholly in that surface.

Figure 22:
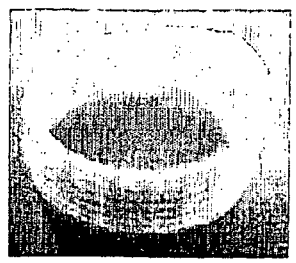
FIG. 22 shows a digital photograph of a chitosan scaffold after freeze drying. This scaffold has been fabricated to validate the ability of the cryogenic prototyping method to fabricate three-dimensional scaffolds. It is a simple tubular structure fabricated by dispensing a single polymer thread in a circular path, the three-dimensional structure is obtained by moving up the z axis and dispensing a similar path directly on top of the previously frozen thread. The pores obtained are aligned in the z axis in the direction of the temperature gradient.

In another example of this method the three-dimensional scaffold is formed by a single lane of polymer solution which is dispensed as a continuous lane into the reaction chamber until the three-dimensional scaffold is formed. In other words, the second and further lanes are made of the first lane of polymer solution which is dispensed continuously without interruption of the first lane. For example, a circular scaffold as illustrated in FIG. 22 can be manufactured by one continuous lane of polymer solution which is continuously dispensed in a spiral manner into the reaction chamber. The lane of the first plane will be lying next to the lane of the next plane and will be in contact with the previous lane at one side without that dispensing of the first lane needs to be interrupted. In another example, the lane of one plane is dispensed as one continuous lane without interruption even when the direction of the dispensed polymer solution is changing.

In another aspect, the present invention is directed to a method of fabricating a three dimensional scaffold suitable for tissue-engineering having a controlled micro- and macroporous structure using cryogenic prototyping comprising:
  a) dispensing multiple threads or drops of a first polymer solution into a reaction chamber to form a first plane;
     wherein the first polymer solution comprises a first polymer and a first solvent;
     wherein the reaction chamber has a first temperature which is at or below the freezing point of the first solvent;
  b) dispensing multiple threads or drops of a second polymer solution into the reaction chamber to form a second plane;
     wherein the second polymer solution comprises a second polymer and a second solvent;
     wherein the second threads or drops are in contact with the deposited threads or drops of the first plane but are laterally shifted in any direction with respect to the threads or drops forming the first plane when they are dispensed into the reaction chamber;
     wherein the reaction chamber has a second temperature, wherein the second temperature is the same or different from the first temperature as long as it is at or below the freezing point of the second solvent;
  c) dispensing multiple threads or drops of a third polymer solution into the reaction chamber to form a third plane;
     wherein the third polymer solution comprises a third polymer and a third solvent;
     wherein the third threads or drops are in contact with the deposited threads or drops of the second plane but are laterally shifted in any direction with respect to the deposited threads or drops of the first plane when they are dispensed into the reaction chamber in the same direction as the first plane;

wherein the reaction chamber has a third temperature, wherein the third temperature is the same or different from the first and/or second temperature as long as it is at or below the freezing point of the third solvent;

d) dispensing further threads or drops of polymer solutions into the reaction chamber to form further planes by repeating steps a) to c) to obtain the three-dimensional scaffold;

wherein the macroporous structure of the scaffold is defined by controlling within one plane the distance of at least some of the multiple threads or drops to each other;

wherein the macroporous structure of the scaffold is defined by controlling the temperature of the reaction chamber when dispensing the polymer solutions into the reaction chamber; and e) removing the solvent of the three-dimensional scaffold.

Figure 10:
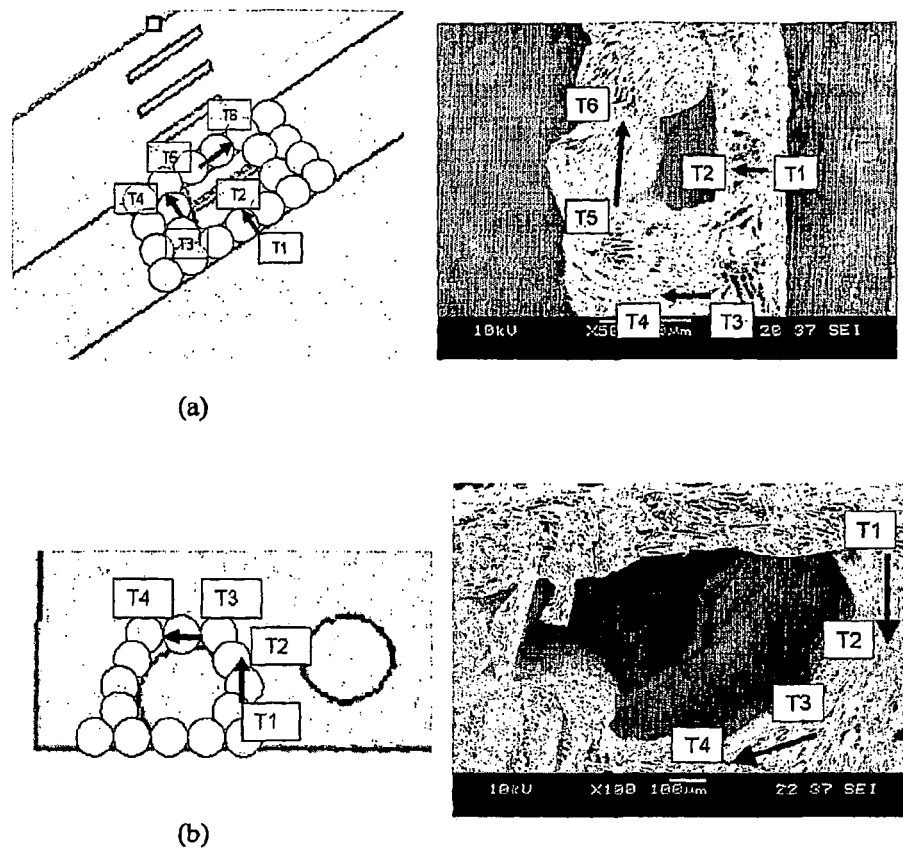
FIG. 10a shows the cross section of a scaffold CAD design with the polymer lanes represented with circles. Due to deposition path, temperature gradients $\Delta T1T2$, $\Delta T3T4$ and $\Delta T5T6$ are created. $\Delta T1T2$, $\Delta T3T4$ are the temperature gradients between lanes deposition at different z coordinates in different planes. $\Delta T5T6$ is in the lateral direction (x axis) as the lanes are deposition over a space (internal channel) so in this example there is no contact with previous z plane. The temperature gradient that results is due to the contact with the polymer lane beside (contact angle 90°). As seen in the SEM micrographs, the micropores are oriented in the direction of temperature gradients.
FIG. 10b shows a similar design of an internal channel. The internal channels shown in FIG. 10 represent the macroporous structure.

Examples for the assembly of such a scaffold are given, for example, in FIG. 10.

These methods allow for the first time the manufacture of scaffolds in one passage having defined micro and macroporous structures.

"Scaffold" or "three-dimensional (3D) scaffold" has the meaning known in the art of tissue engineering which is described in the first paragraph of the background section.

Figure 1:
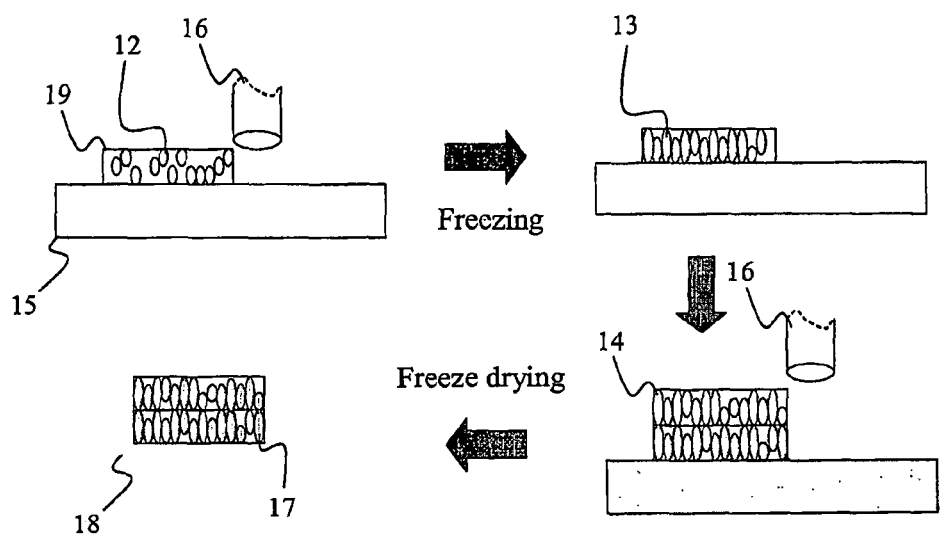
FIG. 1 shows a schematic illustration of the main principles of the cryogenic prototyping process which is based on phase separation between polymer and solvent to form the micropores. The feeding pipe or pipes 16 are guided according to the programmed CAD design over the surface of the cooled reaction chamber 15 and deposit the polymer solution 19 comprising the polymer and the solvent. Upon contact with the surface of the reaction chamber the first lane of polymer solution is starting to freeze. Thus, phase separation between polymer and solvent takes place and the solvent starts to form crystals 12 (transparent cones). After freezing, phase separation is completed and the crystals have been completely formed 13 (opaque cones) within the lane. The space now occupied by the crystals will later faun the micropores. In a next step the feeding pipe 16 is depositing a further lane of polymer solution next to the first lane or in a laterally shifted manner above the first lane. After contact with the frozen surface of the first lane phase separation takes place and crystals form from the solvent 14 (transparent cones). After the desired shape is obtained the scaffold will be subjected to freeze drying to obtain the ready-to-use scaffold 18. In the scaffold 18 the opaque cones 17 represent the micropores.

The controlled creation of micropores in the scaffolds manufactured by the method of the present invention is based on the principle of phase separation upon freezing of a solution comprising a polymer dissolved in a solvent. To achieve phase separation between solvent and polymer the temperature of the reaction chamber is lowered to or below the freezing point of the solvent. Once a polymer solution having room temperature (normally between about 20 to about 25° C.) is dispensed into the cooled reaction chamber, the solvent in the polymer solution will start to separate from the dissolved polymer and form crystals. These crystals are then removed by sublimation during, for example a freeze-drying step, leaving interstices in the material in the spaces previously occupied by the crystals (see FIG. 1).

Figure 14:
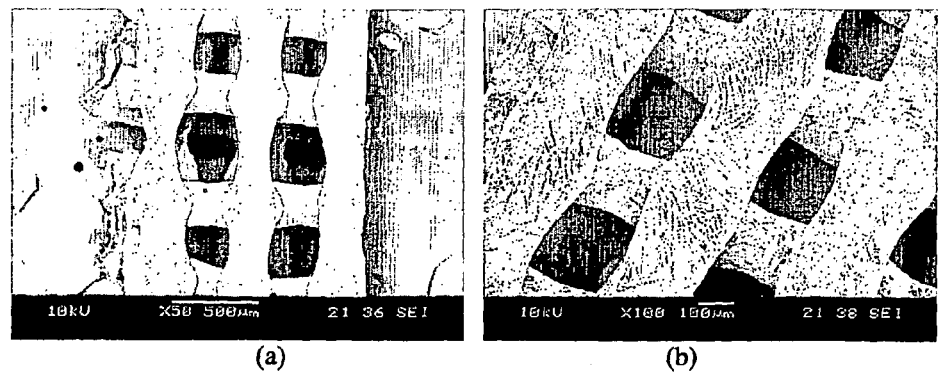
FIG. 14 shows SEM micrographs of PLA mesh scaffold fabricated (a) with needle diameter 0.3 mm and gap 0.6 mm, at magnification ×50 and (b) with needle diameter 0.2 mm and gap 0.3 mm, at magnification of ×100.
Figure 21:
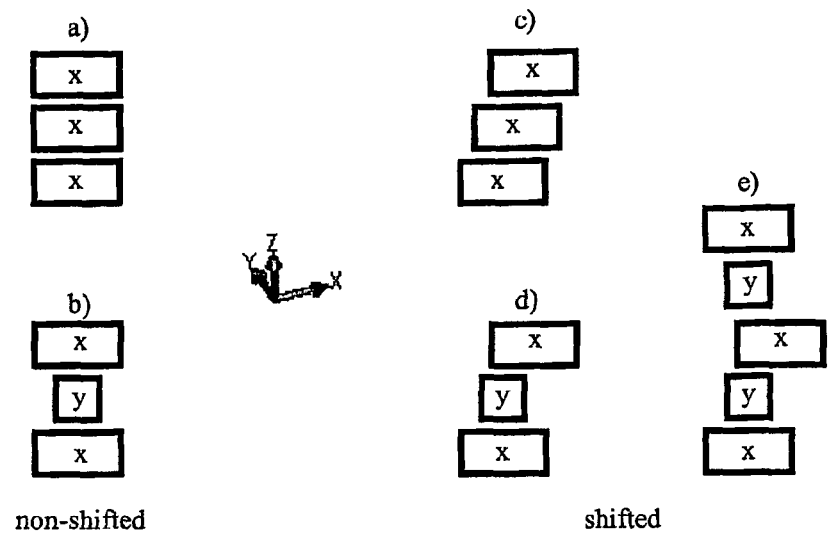
FIG. 21 is supposed to illustrate the meaning of "laterally shifted" and "laterally shifted in any direction" for three-dimensional scaffolds manufactured according to claim 2.
Figure 21:
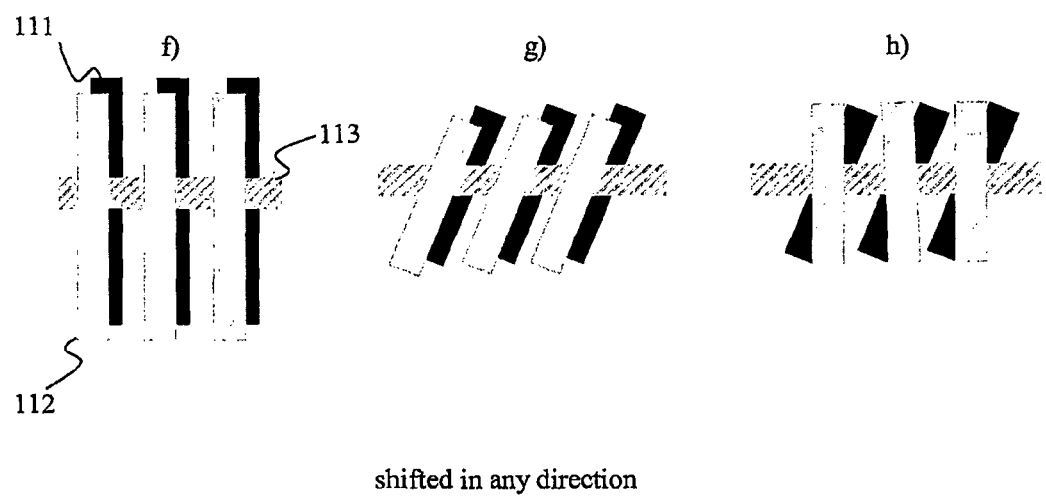

In one method of the present invention the different polymer threads or drops can be laterally shifted to each other in any direction. "Laterally shifted" means that one thread or drop is staggered with respect to another thread or drop as illustrated in FIG. 21 c. With laterally shifted "in any direction" is meant that the thread or drop can be staggered in any direction with respect to another thread or drop of another plane. The numbering of the threads given in FIG. 21 f also applies for FIG. 21 g and h. FIG. 21 h illustrates the meaning of the phrase "in any direction" when comparing FIG. 21 h with FIG. 21 for g. In FIGS. 21 f and g layer 112 is staggered parallel with respect to thread 111 in another plane. With "any direction" it is meant that one thread in one plane, e.g. thread 112, can not only be staggered parallel to another thread in another plane, e.g. thread 111, but can also be staggered in any other direction as for example threads 111 and 112 in FIG. 21 h. FIG. 21 a and b illustrate embodiments in which the different polymer threads are not shifted. The structure of FIG. 21 b is reflected in FIG. 14 a and b which shows a simple grid pattern as known in the prior art (see for example Yan, Y., Xiong, Z., et al., 2003, supra). In FIG. 10 the "laterally shifted in any direction" feature is illustrated on the basis of SEM pictures of scaffolds. The way of constructing those scaffolds is illustrated in the schematic drawing next to the SEM picture in FIG. 10. FIG. 10 illustrates the position of drops of polymer solutions relative to each other in different planes.

One important factor that influences the shape and size of the crystals and thus the micropores formed afterwards is the temperature in the reaction chamber, i.e. the freezing temperature. In general, the temperature in the reaction chamber can be between about 30° C. to about −196° C. or about −50 to about 0° C. In another example, the temperature is between about −30 to about −5° C. or about 0° C.

For example, water has a freezing point of 0° C. at atmospheric pressure. Just below freezing, at temperatures near T=−2° C., the growth of ice crystals is plate-like, with thick plates at lower supersaturations, thinner plates at intermediate supersaturations, and plate-like dendritic structures at high supersaturations. For temperatures near T=−5° C., the growth is columnar, with stout columns at the lower supersaturations, more slender, often hollow columns at intermediate supersaturations, and clusters of thin, needle-like crystals at higher supersaturations. Colder still, near T=−15° C., the growth again becomes plate-like, and again one sees increasing structure with increasing supersaturation. Finally, at the lowest temperatures the growth becomes a mixture of thick plates at low supersaturations and columns at higher supersaturations. Growth of heavy water ($D_2O$) crystals produces similar morphologies as a function of temperature, except shifted by approximately four degrees, in keeping with the isotopic shift in the freezing point between $D_2O$ and $H_2O$ (Libbrecht, K. G., 2005, Reports on Progress in Physics, vol. 68, p. 855-895).

As it is known to a person skilled in the art, crystal growth can be further enhanced when one lets air flow over a growing surface of crystals, a phenomenon called the ventilation effect. This allows using temperatures of, for example −2° C. but achieving the same effect as at a temperature of −4° C.

Since the question of freezing depends also on the pressure in the surrounding atmosphere, the pressure can be increased or decreased to support formation of solid crystals even at higher temperatures. Which pressure and temperature is most suitable to ease the phase separation during freezing of the solvent can be easily determined by a person skilled in the art when looking at the phase diagram of the solvent or mixture of solvents which is supposed to form crystals in the reaction chamber.

In general it can be said that the crystals are growing bigger the smaller the temperature difference between the polymer solution and the reaction chamber (temperature gradient) is. For example, for a solvent like water that would mean that the crystals are growing bigger when the temperature is about −5° C. compared to about −45° C. because at −5° C. the water freezes not so fast and thus the crystals are growing bigger. However, at −45° C. water freezes much faster and thus the crystals do not have the time to grow (see FIG. 11). Thus, the temperature can not only be used to influence the shape of the crystals but also their size.

The micropores which can be formed using this feature can be in a range of about 1 μm to about 1 mm or about 35 to about 90 μm. For example, pore size obtained for chitosan scaffolds range from about 35 to about 90 μm for processing temperatures from −5 to −45° C. In one example, for a processing temperature of −45° C., the ice crystals are formed in 34 seconds, the resulting pore size obtained is about 35 μm. At −30° C., the time taken is around 65 seconds, forming pore sizes of about 60 μm. While at −20° C., ice crystal formation takes about 90 seconds which results in pores of about 75 μm. Lastly, at −5° C., ice crystal formation takes about 167 seconds, resulting in pore size of about 90 μm. However, such values are only exemplary and might change depending on the polymer solution, dispensing pressure, needle size, dispensing speed and other factors which will be discussed further below.

The advantage of the methods used herein is also that the variable setting of the temperature of the reaction temperature allows dispensing different lanes, threads or drops of polymer solution which form a plane at different temperatures. Thus, the greater the temperature difference between the polymer solution and the reaction chamber the smaller the crystals and thus the pores will be. This method thus allows manufacturing one scaffold having micropores of different sizes due to the different temperature differences applied between the reaction chamber and the polymer solutions dispensed into the reaction chamber (see e.g. FIG. 15 d).

It is another advantage of the methods of the present invention that it is possible to manufacture scaffolds with continuous micropores having the same or different micropore sizes. FIG. 4 shows the rate of cooling measured at different freezing temperatures which results in different micropore sizes and morphology. A slower rate of cooling, i.e. lower temperature difference between polymer solution and reaction chamber, will result in larger pores and more integration between the different deposited layers. The dotted line in the SEM micrographs of FIG. 4 is placed at the layer interfaces of different planes of polymer solutions. With a slower cooling rate, the newly deposited plane will have a longer time to spread and melt the previous plane more, resulting in a more integrated and continuous porous architecture. The interlayer connectivity improves with slower cooling rate, the pores looks to be continuous across the planes (see FIG. 4 c and d). For a faster rate of cooling, the micropores are smaller and although the micropores are still interconnected, they are not as continuous as at a lower cooling rate (see FIGS. 4 a and b).

In addition, the present invention further comprises using different time intervals between dispensing of different planes into the reaction chamber. This also provides the possibility to interconnect certain areas within one scaffold or purposely block certain areas from each other through raising the cooling rate to bar neighboring micropores from connecting to each other. Continuous pore structure will be important for directing the cellular infiltration; the cells can be aligned along the pores to form a continuous tissue. As for limiting the interconnectivity or continuity between certain planes, this can be applied to certain applications where it is important to form a distinct barrier between certain planes of different cell types. For example, in engineering the esophagus, it is important to align the muscle cells to form a continuous muscle layer. While for the mucosa layer, it is important to have a dense barrier layer for epithelial cells to attach, proliferate and differentiate. Barrier planes or layers may also be required in some applications to constrain specific cells to certain areas of the scaffold.

Thus, the present invention is also directed to a method further comprising dispensing lanes, threads or drops forming a plane into the reaction chamber only after the lanes, threads or drops forming the previous plane are frozen, i.e. phase separation is completed and all solvent formed solid crystals, and subsequently dispensing any further lanes, threads or drops into the chamber. The following lanes, threads or drops forming the next plane can be dispensed into the reaction chamber before the previous lanes, threads or drops forming the previous plane are completely frozen or after the previous lanes, threads or drops forming the previous plane are frozen.

A further option to control the rate of cooling is to adjust not only the temperature of the reaction chamber but also to adjust the temperature of the polymer solution which is normally at room temperature as described above. Changing the temperatures either of the reaction chamber or the polymer solution or both will affect the rate of cooling which will influence the micropore size as well as the interconnectivity of the micropores.

Figure 5:
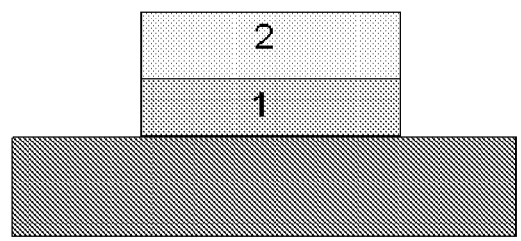
In FIG. 5 one can see that the lane numbered "1" is deposited first while maintained at a certain temperature T1. Subsequently, the polymer can be cooled to a lower temperature T2 before a second polymer solution is deposited on it (lane "2"). Hence, the temperature gradient will be different with that of the previous lane. This results in different rate of cooling for lane 1 and lane 2, which in turn creates lanes with different micropore sizes. By controlling the rate of cooling during the polymer deposition of different parts of the three-dimensional scaffold, different controlled micro architecture can be obtained within the same construct.

Further examples are given to illustrate the features of the methods of the present invention. Again, a scaffold with different micropore size can be fabricated by controlling the rate of cooling during the polymer deposition at different areas of the scaffold. The micropore sizes formed will be different for different rate of cooling, as described above. By varying the rate of cooling for different deposition paths, it will be possible to obtain different micropore sizes within the same scaffold. In FIG. 5 one can see that plane "1" is deposited first while maintained at a certain temperature T1. Subsequently, the polymer can be cooled to a lower temperature T2 before a second polymer solution is deposited on it (plane "2"). Hence, the temperature gradient will be different with that of the previous plane. This results in different rate of cooling for plane 1 and plane 2, which in turn creates planes with different micropore sizes. By controlling the rate of cooling during the polymer deposition of different parts of the three-dimensional scaffold, different controlled micro architecture can be obtained within the same construct.

Figure 6:
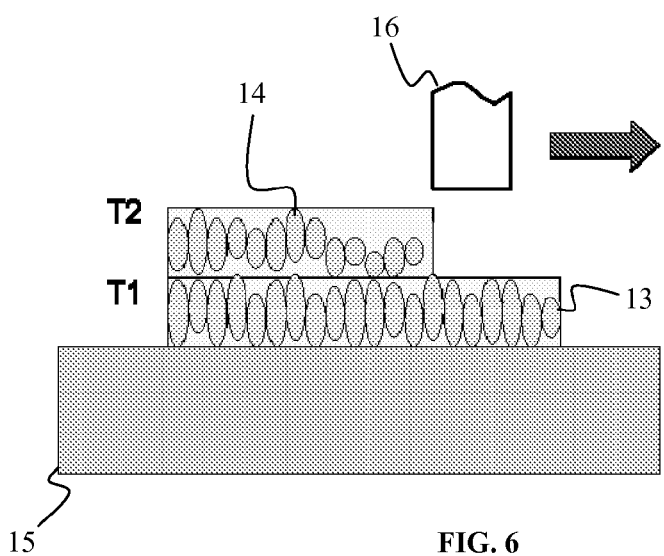
FIG. 6 is an enlarged view of a further embodiment of the third step already shown in FIG. 1. A second lane of polymer solution is deposited at a second temperature above a first lane of polymer solution which has been deposited at another temperature T1. The arrow indicates the direction of movement of the feeding pipe 16. The opaque cones 13 indicate the frozen solvent crystals in the first lane whereas the opaque cones in the second lane 14 indicate the solvent crystals just forming. 15 indicate the surface of the reaction chamber.

In order to control the orientation of the micropores, the direction of the temperature gradient has to be controlled and utilized. To fabricate a three-dimensional scaffold, the cryogenic prototyping process will deposit polymer solution according to a programmed path. As illustrated in FIG. 6, a temperature gradient will be created between the lower temperature (T1) of the frozen polymer plane and the higher temperature of the just deposited polymer plane (T2). This leads to orientation of the frozen crystals during freezing, forming orientated pores. The crystals grow in the direction of the temperature gradient (from cold to warm). As the biopolymer is dispensed, the area in contact with the lanes, threads or drops of the previous plane will start to freeze first. Therefore frozen solvent crystals will start to form at the contacting area and will grow upwards as the entire polymer freezes. After the removal of the crystals by, e.g., lyophilization, the pore orientation obtained will be in the direction of the temperature gradient.

Figure 7:
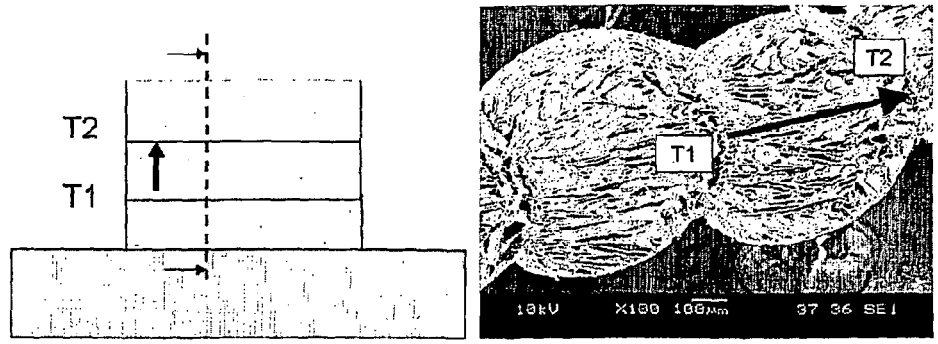
FIG. 7 and FIG. 8 show the direction of the temperature gradients which will be created between the previous lane and the newly deposited lane (indicated by an solid arrow). The SEM picture next to the schemes of FIGS. 7 and 8 show a physical picture of a scaffold in which the direction of crystal growth and thus the micropore orientation is indicated by a solid arrow.

For example, by plotting the different lanes, threads or drops of a plane directly on top of each other (in the z direction) the temperature gradient will be created between the previous lanes, threads or drops of a plane and the newly deposited lanes, threads or drops of the next plane, as seen in FIG. 7. Therefore the micropores will be oriented in the z direction.

Figure 8:
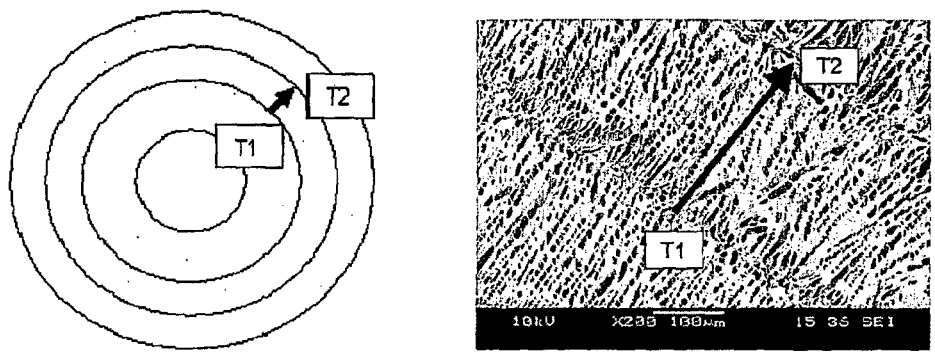

A temperature gradient can also be created in the x and/or y direction. For example, a polymer lane, thread or drop is deposited in a circular path. Subsequently, the next lane, thread or drop is deposited next to the frozen lane, thread or drop in a circular path with a larger radius. The temperature gradient in this case is in the radial direction, between T1 and T2, as seen in FIG. 8. The micropores will be oriented in the radial direction.

When different threads or drops are dispensed into the reaction chamber in an orientation which is shifted between about 0° to 90° with respect to the orientation of the micropores in the previous plane, the micropore orientation can be in the same or any other angle with respect to the micropores in the previous plane. Thus, a temperature gradient will result when the deposited polymer is in contact with a frozen deposited polymer solution having a lower temperature. The method of the present invention utilizes this mechanism to create micropore orientations in the desired direction.

In the design and fabrication of scaffolds, the deposition path of the polymer is programmed to create a temperature gradient in the desired direction, to obtain controlled pore orientations.

FIG. 10 (a) shows the cross section of the scaffold CAD design with the polymer threads represented with circles. Due to deposition path, temperature gradients $\Delta T1T2$, $\Delta T3T4$ and $\Delta T5T6$ are created. $\Delta T1T2$, $\Delta T3T4$ are the temperature gradients between threads deposition at different z coordinates. $\Delta T5T6$ is in the lateral direction (x axis) as the lanes or threads are deposition over a space (internal channel) so in this example there is no contact with lanes or threads of the previous z planes. The temperature gradient that results is due to the contact with the polymer thread beside (contact angle 90°). As seen in the SEM micrographs, the micropores are oriented in the direction of temperature gradients. FIG. 10 (b) shows a similar design of an internal channel.

Figure 9:
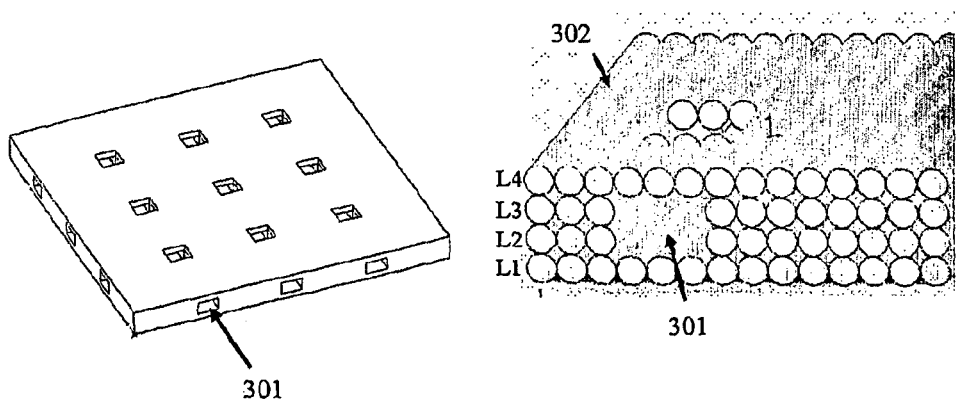
FIG. 9 shows CAD scaffold design with internal channels. To fabricate this scaffold, the CAD design is sliced into 4 layers (FIG. 9 right picture) to be deposited plane by plane in the z axis as illustrated in FIG. 9 (right picture). In the right picture of FIG. 9 one can see that at least some of the lanes 302 in a plane are interrupted to form spaces/gaps 301 which later form the macropores in the scaffold.

For constructs with internal channels, temperature gradients of different orientation can also be created according to different deposition paths. FIG. 9 shows CAD scaffold design with internal channels. To fabricate the scaffold, the CAD design is sliced into 4 planes to be deposited lane by lane in the z axis.

The macropores are thus defined through the path of deposition of the polymer solution. Other than the micropores the macropores are not formed by crystal growth. The size and orientation of the macropores is defined by the deposition path of the lanes, threads or drops of polymer solutions which form the different planes of the scaffold.

To change the macroporous structure of the scaffold, the methods of the present invention further comprise changing the distance between at least some of the lanes, threads or drops which are dispensed in the reaction chamber.

One advantage of the methods of the present invention is that it is able to provide control over macro as well as micro architecture of fabricated scaffold. The rapid prototyping aspect of the plotting will allow the fabrication of customized three-dimensional CAD designs. Micropores of specific size and orientation can be created by the freezing step of the cryogenic prototyping process. Therefore, scaffolds fabricated with the methods of the present invention can be tailored for different tissue engineering requirements. In addition, the use of porogens is eliminated with the methods of the present invention. As these methods make use of the freezing properties of solvents, it can be applied to a wide range of polymer systems. The low operating temperatures will also allow the incorporation of bioactive components such as growth factors and protein which will denature at higher temperatures (see further below).

Other factors which influence the micro and macroporous structure are the thickness of the polymer lanes, threads or drops dispensed and the choice of the solvent used.

The choice of solvent will also affect the rate of cooling. Solvent with a larger latent heat of fusion will take longer to freeze which means a slower rate of cooling. In addition, the mass of polymer dispensed will also affect the rate of cooling. With increase in mass of polymer dispensed, more heat has to be lost before freezing of the solvent can take place. Therefore, a longer time is required for the temperature to drop and the rate of cooling is slower.

The methods of the present invention are therefore further comprise using an organic or inorganic solvent. A solvent can be, for example, 1,1,1,3,3,3-hexafluoroisopropanol (HFIP), acetone, molten phenol, naphthalene, N,N-dimethylformamide (DMF), water, formic acid, acetic acid, lactic acid, ethanol, trifluoroethanol, xylene, diethylformamide, hexafluoro-2-propanol, dioxane, chloroform, dimethylacetamide, dichloromethane, tetrahydrofuran (THF), trifluoroacetic acid, N,N-dimethyl acetamide (DMAc), isopropyl alcohol (IPA), methylene chloride, methyl ethyl ketone, octane, propyl alcohol, pyridine, tetraline, toluene, heptane, hexane, methanol, ethyl ether, ethyl alcohol, ethyl acetate, dichloroethyl, carbon tetrachloride, cresol, chlorobenzene, cyclohexane, n-butyl alcohol, butyl acetate, benzyl alcohol, benzene, sulphuric acid or hexafluoro isopropanol, HFIP and mixtures thereof. In one example of the present invention, an inorganic solvent used is acetic acid or water whereas in other examples dioxane, benzene, cyclohexane, carbon tetrachloride or ethylene glycol is used as organic solvent. Inorganic solvents are, for example, acetone, water/chloroform, water or sulphuric acid. Examples for organic solvents are methylene chloride, 1,1,1,3,3,3-hexafluoroisopropanol (HFIP), molten phenol, naphthalene, methyl ethyl ketone, octane, propyl alcohol, pyridine, tetraline, toluene, heptane, hexane, methanol, ethyl ether, ethyl alcohol, ethyl acetate, dichloroethyl, carbon tetrachloride, N,N-dimethylformamide (DMF), formic acid, acetic acid, lactic acid, ethanol, cresol, chlorobenzene, cyclohexane, n-butyl alcohol, butyl acetate, benzyl alcohol, benzene, diethylformamide, hexa-fluoro-2-propanol, dichloromethane mixed with trifluoroacetic acid, dioxane, chloroform, dimethylacetamide, dichloromethane, tetrahydrofuran (THF), N,N-dimethyl acetamide (DMAc), HFIP mixed with DMF, isopropyl alcohol (IPA) or hexafluoro isopropanol. Further organic solvents can be found in Vogel's Textbook of Practical Organic Chemistry (5th Edition, 1996, Prentice Hall). The above list is not meant to be limiting and further examples of suitable solvents will be known to a person skilled in the art.

On the other hand, the thickness of the lane, thread or droplet is influenced by the dispensing speed, the size of the orifice of the dispenser and the pressure with which the polymer solution is dispensed into the reaction chamber.

Thus, in another aspect the methods of the present invention further comprise varying the thickness of the lanes, threads or drops of the dispensed polymer solution by using at least one needle for dispensing the polymer solution having varying diameters for the outlet opening of the at least one needle. The larger the outlet opening of the feeding pipe is the larger the diameter of the lane, thread or drop of the polymer solution. In one aspect the diameter of the outlet of the at least one needle is in a range of about 0.1 mm to about 1 or 2 mm. Commonly used sizes are 0.15, 0.2 and 0.3 mm.

In another aspect the methods of the present invention further comprise varying the speed with which the at least one needle for dispensing the polymer solution into the reaction chamber is moved above the surface of the reaction chamber. The faster the step motor moves the feeding pipe over the reaction chamber the thinner the polymer lanes, threads or drops will be. Another option to influence the thickness of the lanes, threads or drops (droplets) is by varying the dispensing pressure. Therefore, the methods of the present invention further comprise changing the pressure with which the polymer solution is dispensed into the reaction chamber. The higher the pressure is the thicker the lanes, threads or droplets which are dispensed through the feeding pipe into the reaction chamber.

Figure 2:
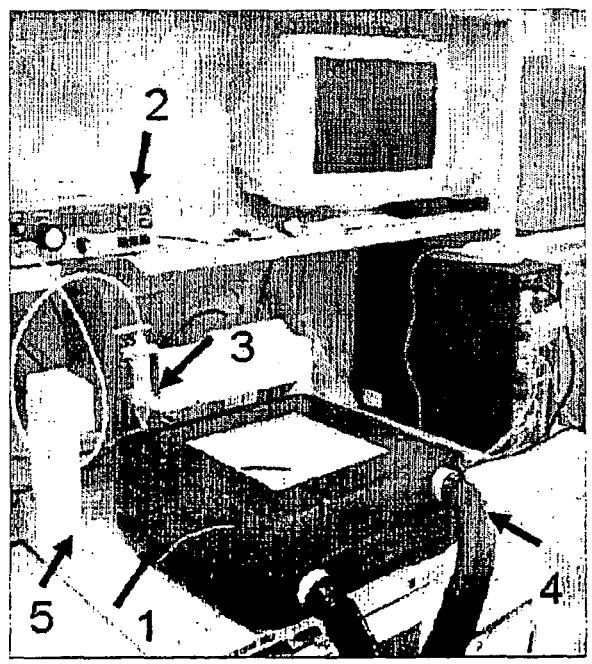
FIG. 2 shows a digital photograph of the apparatus used to manufacture the scaffolds according to the method of the present invention. The equipment consists of a cryogenic chamber 1 which is cooled by coolant from an external refrigerated circulator (Julabo F83-HL). The circulator is able to maintain the circulating coolant at temperatures in the range of −83 to about −50° C. However, with other equipment temperatures can be cooled below these points. The coolant from the circulator is run though the cryogenic chamber via the cooling pipes 4. Polymer solution is dispensed through a nozzle 3, into the cryogenic chamber. The chamber and nozzle is mounted on a x, y, z axis table 5 (Musashi Shotmaster 300) which is computer controlled to move in a programmed path. The mounted nozzle moves in the x and z axis while the chamber moves in the y axis. The on and off control of dispensing and the dispensing pressure is controlled by the dispenser 2 (Musashi Super Σx dispenser). The dispenser is also computer controlled to control the dispensing of polymer. MuCAD software is used to control the dispenser and the x, y, z table, this is the program provided by Musashi to interface with the dispensing unit.
Figure 3:
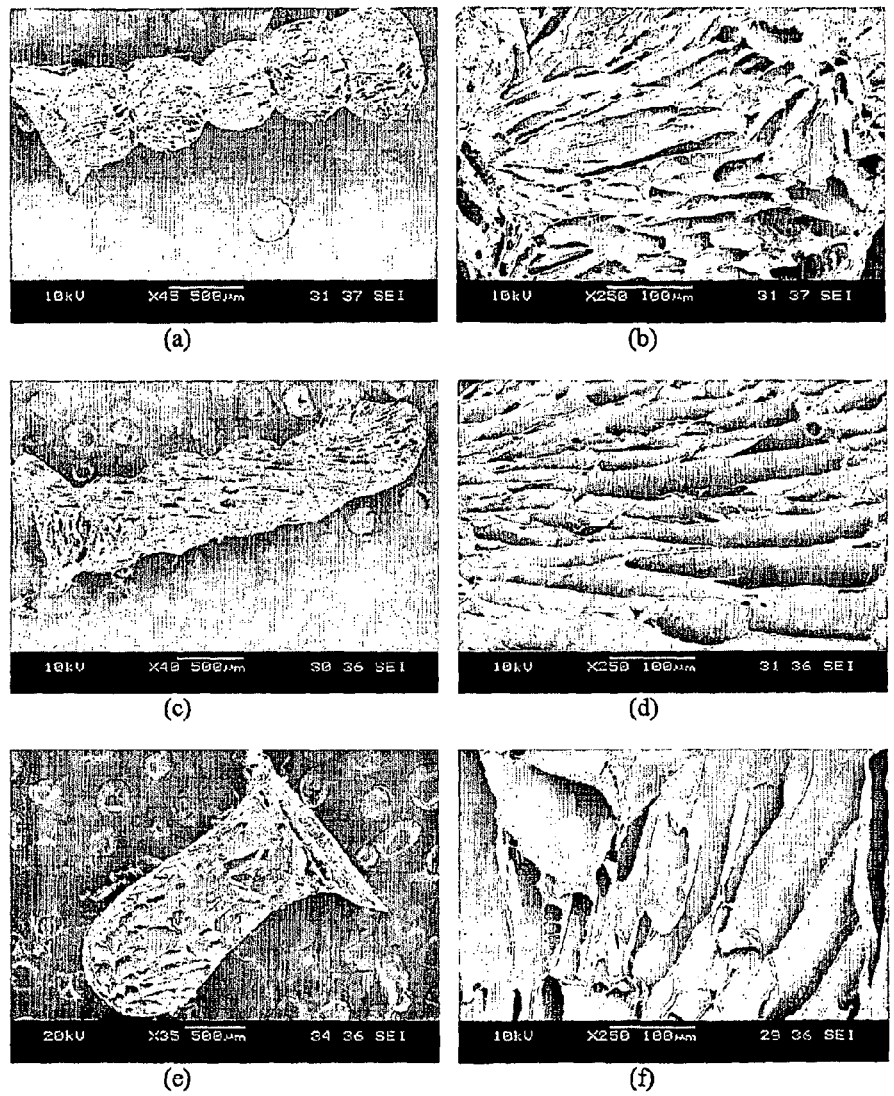
FIG. 3 shows SEM micrographs of cross section profiles of chitosan scaffolds fabricated at (a) −45° C. at magnification ×45, (b) −45° C. at magnification ×250 (c) −25° C. at magnification ×45, (d) −25° C. at magnification ×250, (e) −5° C. at magnification ×45, and (f) −5° C. at magnification ×250. From picture 3a it can be seen that at temperatures about −45° C. the microporous structure is not continuous but the separate polymer drops are separated from each other. The higher the selected temperature (see FIG. 3 c and e) the more continuous the microporous network becomes.
Figure 4A:
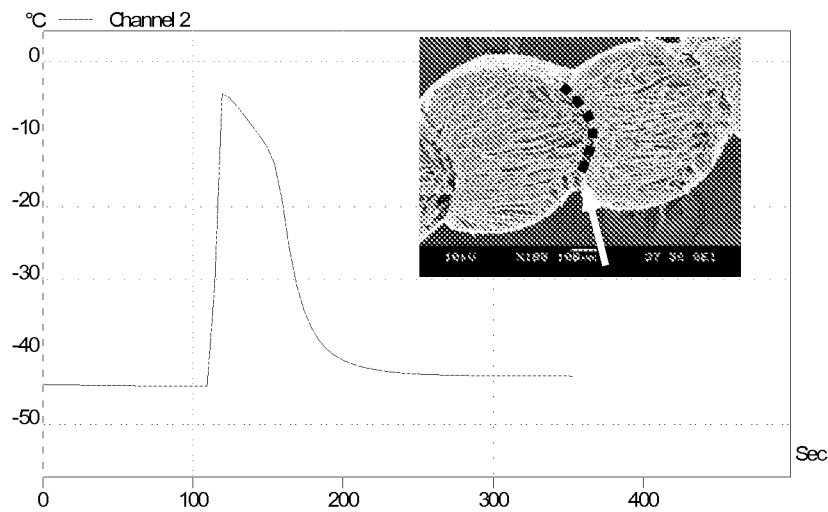
FIG. 4 shows cooling curves at different processing temperatures of (a) −45° C., (b) −30° C., (c) −20° C. and (d) −5° C. Similar to FIG. 3, FIG. 4 demonstrates that a slower rate of cooling, i.e. lower temperature difference between polymer solution and reaction chamber, will result in larger pores and more integration between the different deposited lanes. The dotted line in the SEM micrographs of FIG. 4 is placed at the lane interfaces of different lanes of polymer solutions. Whereas the interconnection is very poor at −45° C., the different sections of the scaffold are more interconnected at temperatures between about −30° C. to −5° C.
Figure 4B:
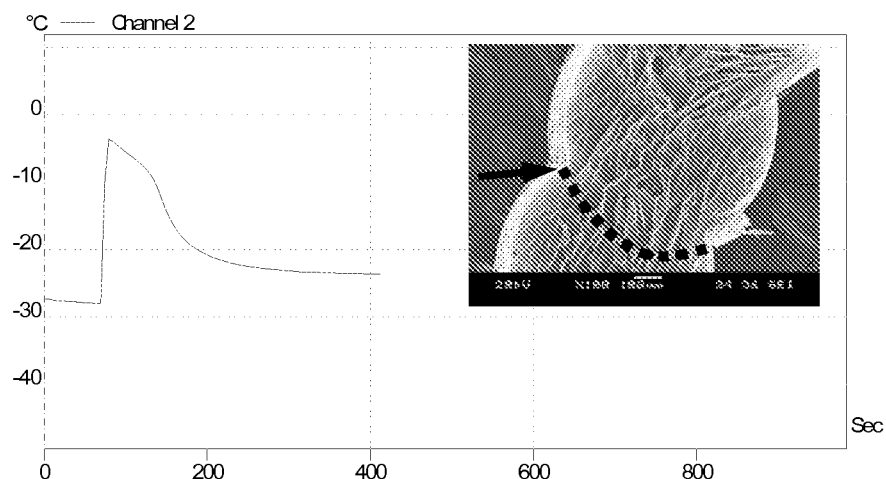
Figure 4C:
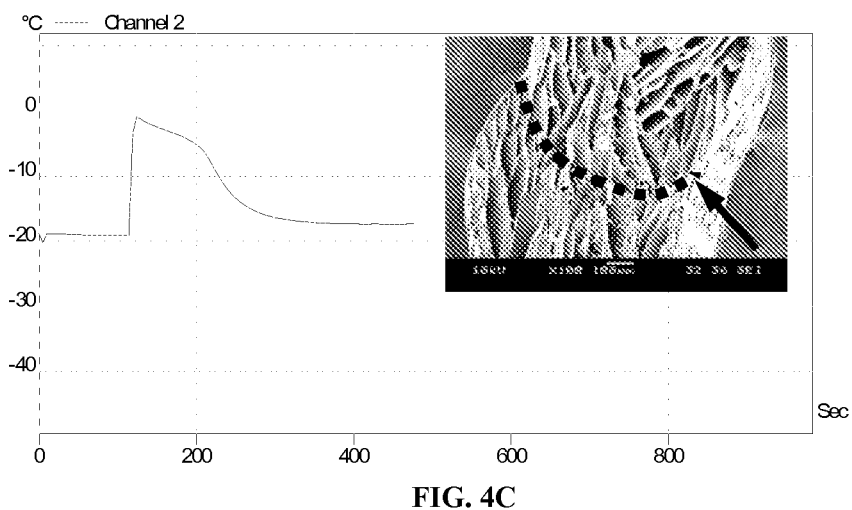
Figure 4D:
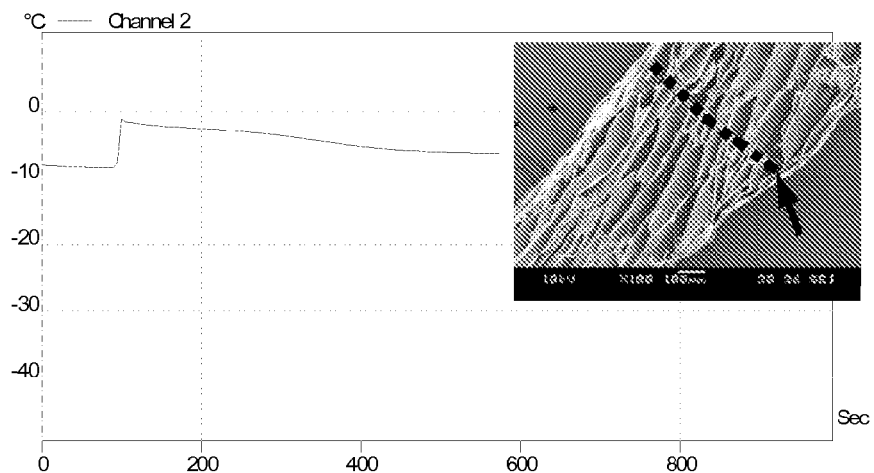
Figure 27:
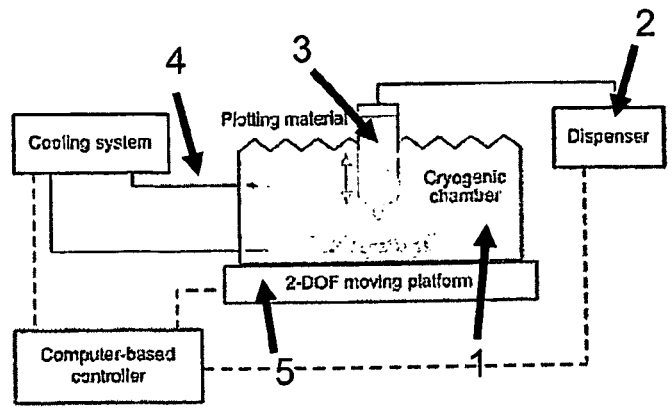
FIG. 27 shows a schematic illustration of the same apparatus shown in FIG. 2.

The polymer solution can be dispensed through the feeding pipe of a prototyping apparatus into the reaction chamber by way of continuous deposition (i.e. depositing threads or lanes) or by drop-on-demand deposition (i.e. deposition of drops) or a combination of both deposition types (Liu, Q., Sui, G., Leu, M. C., 2002, supra). Which type is preferred will depend on the 3-D physical model which is build up plane by plane by the prototyping apparatus. An example of a prototyping apparatus is illustrated in FIGS. 2 and 27. The exemplary apparatus shown in FIGS. 2 and 27 is using one feeding pipe. However, it is also possible to use a prototyping apparatus having more than one feeding pipe, namely 2, 3, 4, 5 or even more feeding pipes.

The specific dimensions of the reaction chamber underlie no specific requirements as long as the reaction chamber can be cooled and is big enough to house the scaffold or scaffolds to be manufactured in it. The bottom of the reaction chamber is in general flat and is made of metal, ceramics, and different kinds of plastics or glass. However, it is also possible to use reaction chambers with another surface shape or to locate further forms in the reaction chamber onto which the scaffold is supposed to be dispensed. For example, it might be desirable to locate a hollow rotatable mandrel in the reaction chamber onto which the scaffold is supposed to be dispensed. An example for a possible reaction chamber is shown in FIG. 2.

The desirable characteristics of suitable polymers which can be used in the methods of the present invention are biocompatibility (i.e. not provoke any unwanted tissue response to the implant, and at the same time to possess the right surface chemistry to promote cell attachment and function) and biodegradability (i.e. degradable into nontoxic products, leaving the desired living tissue). Potential materials are known to a person skilled in the art and can include polymers, synthetic polymers and ceramics.

Suitable ceramics can be, for example, α-tricalcium phosphate, β-tricalcium phosphate which are both biodegradable. Further examples of suitable polymers would be collagen, poly(D,L-lactide) (PLA), poly(urethanes), poly(siloxanes), poly(silicones), poly(ethylene), poly(vinyl pyrrolidone), poly(2-hydroxy ethyl methacrylate), poly(N-vinyl pyrrolidone), poly(methyl methacrylate), poly(vinyl alcohol) (PVA), poly(acrylic acid), poly(vinyl acetate), polyacrylamide, poly(ethylene-co-vinyl acetate), poly(ethylene glycol), poly(methacrylic acid), polyglycolic acids (PGA), poly(lactide-co-glycolides) (PLGA), nylons, polyamides, polyanhydrides, poly(ethylene-co-vinyl alcohol) (EVOH), polycaprolactone, poly(vinyl acetate), polyvinylhydroxide, poly(ethylene oxide) (PEO), polyorthoesters, chitosan, cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, and copolymers or physical blends of these materials. In one example, chitosan or PLA is used as biodegradable polymer. Chitosan can, for example, be dissolved in acetic acid whereas PLA can be dissolved, for example in dioxane.

As previously mentioned, it is possible to add further substances, for example at least one bioactive substance, to the polymer solution used in the methods of the present invention to promote growing of neo-tissue in the scaffold.

In particular substances which can support the ingrowth of cells into the scaffold can be incorporated. Those components can be applied either by mixing them directly with the polymer solution or by applying the additional components simultaneously or subsequently onto the scaffold. For example, biological molecules such as fibronectin and laminin can be incorporated within the scaffold matrix to promote cellular activities such as attachment and migration. The final freeze-drying step serves to lyophilize the molecules, which might help to preserve the proteins in the matrix.

It is further possible to enhance attachment of cells to the biocompatible or biodegradable substrate by coating the scaffold matrix with bioactive substances such as basement membrane components, agar, agarose, gelatin, gum arabic, collagens, fibronectin, laminin, glycosaminoglycans, mixtures thereof, and other materials having properties similar to biological matrix molecules known to those skilled in the art of cell culture. Mechanical and biochemical parameters ensure the matrix provide adequate support for the cells with subsequent growth and proliferation. Factors, including nutrients, growth factors, inducers of differentiation or dedifferentiation, products of secretion, immunomodulators, inhibitors of inflammation, regression factors, biologically active compounds which enhance or allow vascular ingrowth or ingrowth of the lymphatic network or nerve fibers, and drugs, can be incorporated into the matrix of the scaffold or provided in conjunction with the matrix. Similarly, polymers containing peptides such as the attachment peptide RGD (Arg-Gly-Asp) can be synthesized for use in forming matrices.

Removing the solvent from the scaffold takes place by freeze-drying (also known as lyophilization) or sublimation or liquid exchange. Freeze drying works by freezing the material and then reducing the surrounding pressure and adding enough heat to allow the frozen compound in the material to sublime directly from the solid phase to gas.

Different kinds of freeze dryers can be used for the purposes of the present invention, such as rotary evaporators, manifold freeze dryers, or tray freeze dryers.

Optionally it is possible in the methods of the present invention to include a further step of drying the scaffold after the freeze-drying step to remove residual solvent which still remained in the scaffold.

The present invention also refers to the use of a method of the present invention for the manufacture of a scaffold for tissue engineering. In another aspect the present invention refers to a scaffold obtained by a method of the present invention.

Even though the scaffolds obtained via the method of the present invention might also be used outside the field of tissue engineering, they are preferably used for tissue engineering purposes. Therefore, the scaffold of the present invention might be seeded with one or more eukaryotic cell lines. Depending on the tissue which the applicant wishes to develop in and on the scaffold a person skilled in the art will know which cell line or cell lines can be seeded onto the scaffold. As previously mentioned it is also possible to add further bioactive substances to the scaffold to enhance development and growing of cells seeded on the scaffold.

For example, esophageal smooth muscle cells and epithelial cells are used for esophageal tissue engineering. Fibroblasts and keratinocytes are used for skin tissue engineering. Myoblasts with endothelial cells are used to engineer vascularized skeletal muscle tissue.

For example, the scaffolds of the present invention can be seeded with fibroblasts for skin regeneration or bone marrow stem cells for bone development. In another example, in a scaffold which is used for tissue engineering of the esophagus, it is important to have epithelial cells to form the mucosa layer which acts as the barrier to the transit of food. Smooth muscle cells are also required to re-create the muscle layer of the esophagus.

The scaffolds can be used to provide an ECM like structure which supports cell growth and thus regeneration of the damaged tissue. It can also be used in applications which require high cell density and the presence of vasculatures such as engineered muscle tissues (Levenberg, S. et al., 2005, supra).

The scaffolds can also be used for localized delivery of therapeutic agents as well as controlled release of such agents at the target site in a subject.

By "consisting of" is meant including, and limited to, whatever follows the phrase "consisting of". Thus, the phrase "consisting of" indicates that the listed elements are required or mandatory, and that no other elements may be present.

By "comprising" it is meant including, but not limited to, whatever follows the word "comprising". Thus, use of the term "comprising" indicates that the listed elements are required or mandatory, but that other elements are optional and may or may not be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXAMPLES

Control of Micropores—Effect of Temperature on Micropore Size and Orientation

In order to control the micropore size and orientation, experiments are carried out to study the effect of different process parameters. The most significant parameter in controlling the micropore size is the temperature difference between the solution and the chamber ($\Delta T$). For a larger $\Delta T$, the rate of freezing is faster which results in smaller frozen solvent crystals. In the case of a smaller $\Delta T$, the frozen crystals will be larger as the rate of freezing is now slower. The examples below show that this mechanism is valid for both aqueous and organic based polymer solutions, illustrating the versatility of the rapid freeze prototyping (RFP) process.

Aqueous Based Solvent (Chitosan Solution in Acetic Acid)

Figure 11:
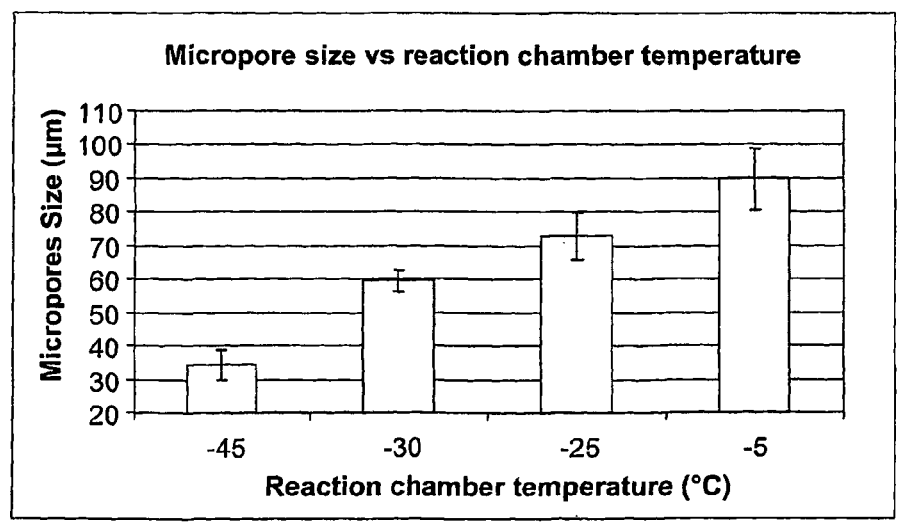
FIG. 11 shows the effect of chamber temperature on micropore size for chitosan scaffolds. The temperatures which have been used when dispensing a chitosan/acetic acid solution into the reaction chamber were −5, −25, −30 and −45° C. It can be observed that with increasing chamber temperature and decreasing $\Delta T$, larger pore sizes are obtained. Pore sizes from 35 μm (−45° C.) up to 90 μm (at −5° C.) can be obtained by increasing the chamber temperatures from −45 to −5° C. At −30° C. the micropore size is about 60 μm whereas the micropore size at −25° C. is about 73 μm. The average pore size is measured from SEM micrographs using the provided software SMile View (SEM model JSM-5600LV, JEOL). 5 measurements are taken 3 numbers of micrographs per temperature sample. The average and standard deviation is then calculated, the standard deviation (SD) bar can be seen in the graph. For −45° C., SD=4.3, −30° C., SD=3.2, −25° C., SD=7.1, −5° C., SD=8.6.

4% wt./vol. chitosan solution (in 2% acetic acid), maintained at 23° C., is dispensed according to the dispensing path illustrated in FIG. 7 and frozen at chamber temperatures of −5, −25, −30 and −45° C. to obtain scaffolds of different micropore sizes. FIG. 11 shows the effect of chamber temperature on micropore size for chitosan scaffolds. It is observed that with increasing chamber temperature and decreasing $\Delta T$, larger pore sizes are obtained. Pore sizes from 35 µm up to 90 µm can be obtained by increasing the chamber temperatures from −45 to −5° C.

Figure 12:
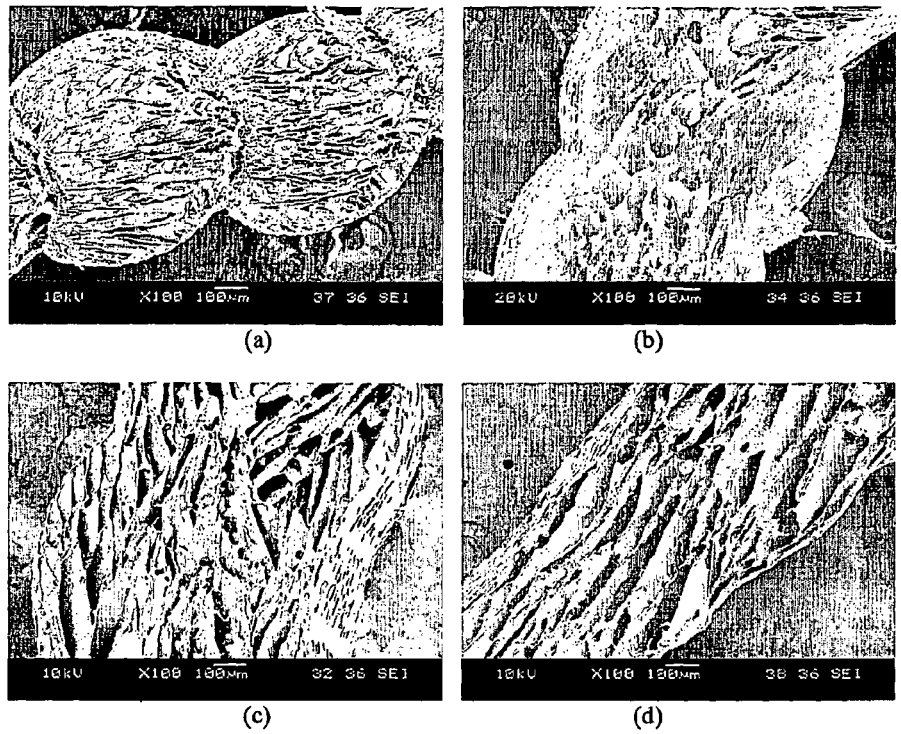
FIG. 12 also shows SEM micrographs of the cross section profile of chitosan scaffolds fabricated at (a) −45, (b) −30, (c) −20 and (d) −5° C., however at magnification of ×100.

FIGS. 12 (a) to (d) show SEM micrographs of the cross section of scaffolds obtained at −45 (a), −30 (b), −20 (c) and −5° C. (d). It can be seen from the Figures that the micropores are orientated vertically in the z-axis, in the direction of the temperature gradient. This is evident throughout the different processing temperatures. The pore size increases with increasing temperature and the structure becomes more open. In addition the interface between different lanes, threads or drops of different planes become less obvious and the pores looks to be more interconnected.

Organic Based Solvent (PLA in Dioxane)

Figure 13:
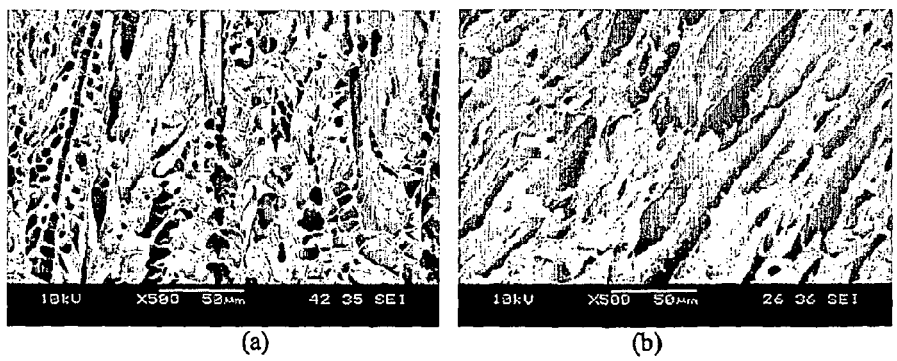
FIG. 13 shows SEM micrographs of cross section profile of PLA scaffolds fabricated at (a) −45 and (b) −10° C., at magnification of ×500. It can be seen that at the same reaction chamber temperature (−45° C.), PLA scaffolds have smaller micropores (~15 μm) as compared to chitosan scaffolds. This can be attributed to water having a higher latent heat of fusion (334 kJ/kg) as compared to dioxane (141 kJ/kg). As water has a higher latent heat, more heat has to be lost before it changes to solid state. At the same chamber temperature, it will take a longer time for water to change to solid state as compared to dioxane. This will result in the formation of larger crystals for water based solvent system. This shows that the choice of solvents can also influence the microporosity of the scaffold.

The RFP method can also be applied to organic solvents. Scaffolds are fabricated using 10 wt./vol. % PLA (in dioxane). The same processing steps as described above for chitosan, was followed for PLA. FIGS. 13 (a) and (b) show SEM micrographs of scaffolds fabricated at −45° C. (a) and −10° C. (b). The same alignment of micropores is observed and micropore sizes also increases with increasing chamber temperature. Dioxane (melting point 11° C.) freezes and its crystals grow in the direction of the temperature, similar to the results obtained with water-based solvent, e.g. chitosan solution in the previous example. After freeze drying, the dioxane crystals are removed by freeze drying and a porous structure is obtained.

The frozen scaffold is transferred to Christ Apha 1-2 freeze dryer to remove the frozen solvent crystals. The freeze dryer is kept at −50° C. and a vacuum is established by a pump which is switched on after the scaffold is placed in the chamber. At low temperature and pressure, the frozen solvent crystals vaporize, leaving behind a porous structure. Low temperature is required as the scaffold has to be frozen to retain the solvent crystal structure. The scaffold is kept in the freeze dryer overnight, and the final porous scaffold can then be removed from the freeze dryer.

Another important observation is that at the same reaction chamber temperature (−45° C.), PLA scaffolds have smaller micropores (~15 um) as compared to chitosan scaffolds. This can be attributed to water having a higher latent heat of fusion (334 kJ/kg) as compared to dioxane (141 kJ/kg). As water has a higher latent heat, more heat has to be lost before it changes to solid state. At the same chamber temperature, it will take a longer time for water to change to solid state as compared to dioxane. This will result in the formation of larger crystals for water based solvent system. This shows that the choice of solvents can also influence the microporosity of the scaffold.

Control of Macrostructure by Computer Aided Design (CAD)

Design of Scaffold According to FIG. 9

With regards to the scaffold with micropores formed in the shape of internal channels 301 (CAD design as seen in FIG. 9), the design of the polymer dispensing path is as seen in the FIG. 9 (right picture). 301 in FIG. 9 refers to the channels incorporated into the design. FIG. 9 (right picture) shows how the polymer lanes are dispensed to fabricate the scaffold (only a portion of the scaffold is shown). The polymer lane is represented as cylindrical tube 302. As seen in 9 (right picture), the three-dimensional scaffold design is sliced into 4 planes (L1-L4), and the polymer is dispensed plane by plane according to the paths as simulated. For each plane, the polymer lanes are dispensed in a straight line and the subsequent lane dispensed after an offset in the y direction. The lane will not be dispensed in areas within one plane where the channels 301 are designed. The next plane will be dispensed on the previous frozen plane in a similar manner according to the design. The pores are aligned in the direction of the temperature gradient created due to the dispensing paths.

Design of Scaffold for Mimicking Esophageal Tissue

The esophagus is a tubular organ which extends from the pharynx to the stomach, its main function being to secrete mucus and transport food to the stomach. FIG. 28 shows the cross section of the esophagus. The innermost layer 401 is the mucosa which is a thick layer of stratified squamous epithelium. Next is the submucosa 402 which contains the mucous secreting glands and loosely connects the mucosa to the muscle layer. The muscularis externa consists of two planes of muscle of different orientation. The inner layer 403 has muscle fibers arranged circumferentially while in the outer layer 404, the fibers are arranged longitudinally. Hence is designing a scaffold for esophageal tissue engineering, it is important to mimic the structure of the esophagus and provide orientation for smooth muscle cells.

Figure 15:
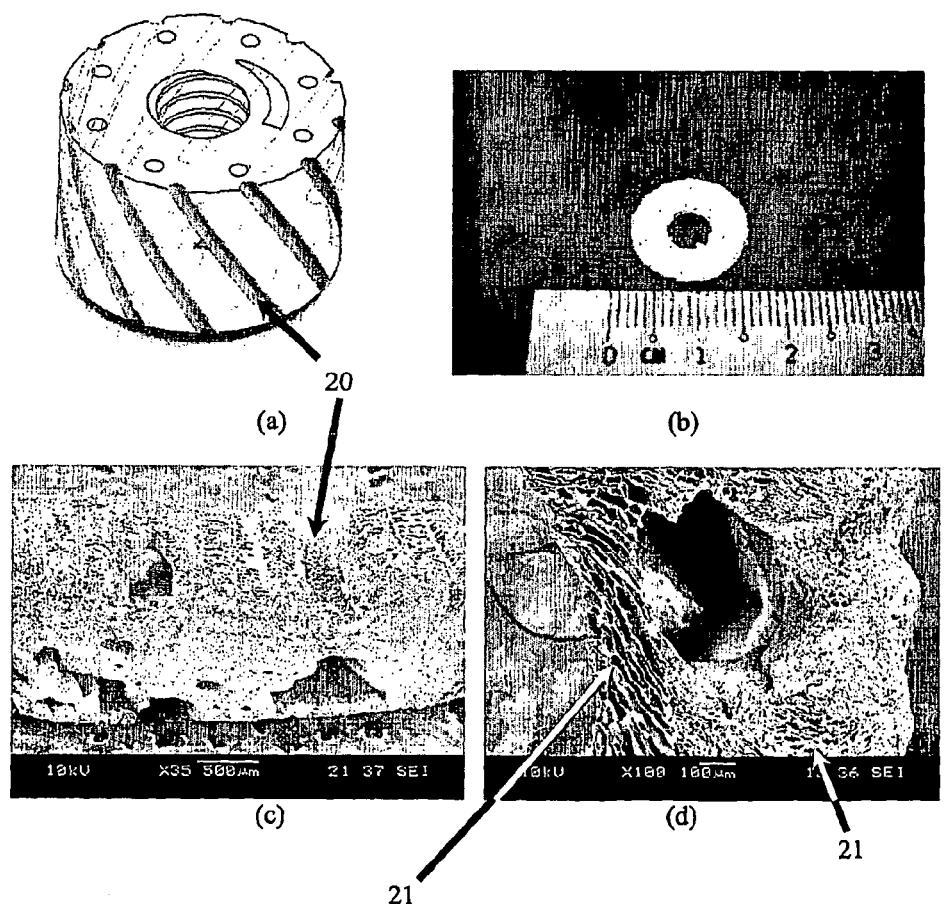
FIG. 15a shows a CAD design of tubular design for esophageal tissue engineering and FIG. 15b shows a digital photograph of the chitosan scaffold of FIG. 15a fabricated with CAD design. SEM micrographs of cross section chitosan scaffolds showing internal macro channels 20 and microporosity 21 of this scaffold, (c) at magnification of ×35 and (d) at magnification of ×100.
In FIG. 15c the macropores (grooves and channels) can be seen which are going around and through the scaffold as indicated in FIG. 15a. At a higher magnification (×100, FIG. 15d) one can see the microporous structure (indicated exemplarily by the two arrows with the number 21) in the polymer threads which form around the micropore 20.
Figure 29A:
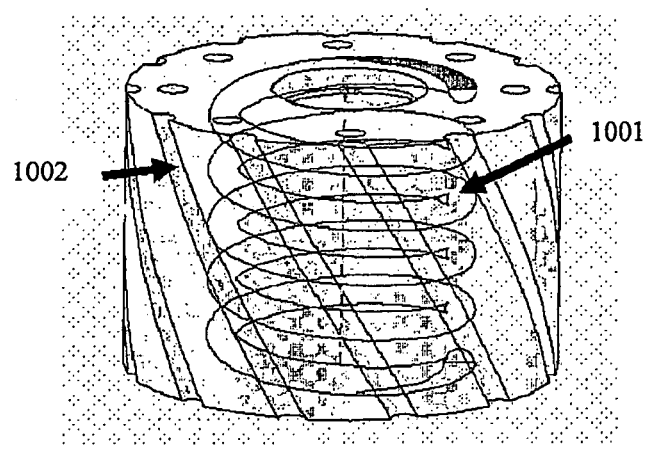
FIGS. 29 a and b show a CAD design of tubular design for esophageal tissue engineering.
FIG. 29c shows a cross section illustrating the dispension path for a portion of the scaffold which is similar to the area marked in the rectangle in FIG. 29b.

FIGS. 15 and 29 show the design of a tubular scaffold for esophageal tissue engineering. The helical channels 20, 1002 are designed to allow orientation of the muscle layer, the inner channels 1001 are oriented circumferentially while the outer channels are oriented longitudinally. FIG. 29a gives a clearer picture of the hidden internal circular channel 1001 within the scaffold and the external longitudinal channels 1002. This mimics the muscle fiber orientation of the esophagus. For the inner most mucosa layer, a dense barrier will be required for epithelial cells to attach, proliferate and differentiate. Hence the inner polymer layer will be denser with smaller pores, which can be fabricated by controlling the rate of cooling (faster cooling rate).

Figure 29B:
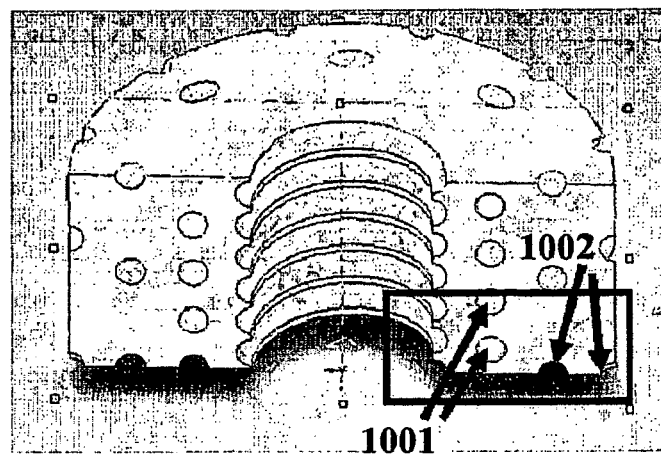
Figure 29C:
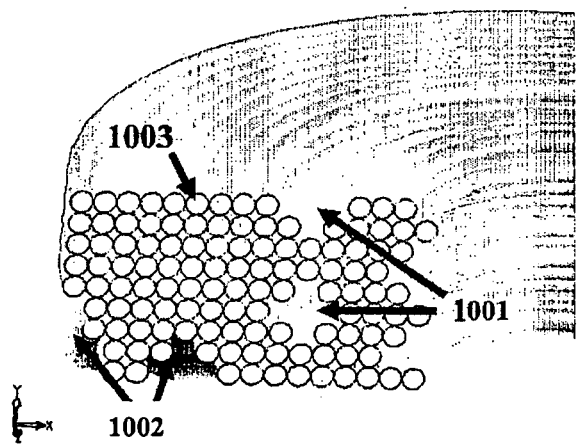

The tubular scaffold is also fabricated plane by plane. FIG. 29b shows the cross sectional view of the CAD design. 1001 is the circular channels while 1002 are the longitudinal channels. FIG. 29c shows the dispensing path for a portion of the scaffold (cross section) which is similar to the area marked in the rectangle in FIG. 29b. In this case the dispensing path of the lanes 1003 is designed to be circular which mimics the natural structure of the esophagus. The polymer is dispensed plane by plane according to the circular paths; channels are formed by not dispensing polymer in that area. Each layer is fabricated by dispensing polymer in a circular path with the subsequent polymer lane dispensed in a circular path with larger radius next to the frozen thread. The next plane is dispensed on top of the frozen plane in a similar fashion. FIG. 15 shows a scaffold fabricated according to this design, the macro and micro porosity can be seen from the SEM micrographs.

Effect of Micro- and Macropore Size and Orientation in Cell-Matrix Interaction (3T3 Fibroblasts)

Chitosan scaffolds fabricated at −45° C. (micropore size ~35 μm) and −5° C. (micropore size ~90 μm) were seeded with 3T3/NIH (murine fibroblast; cell density of $4 \times 10^5$ cells/cm$^2$) fibroblasts. Scaffolds used in this experiment are fabricated according to the dispensing path as shown in FIG. 7. A single polymer thread or lane is dispensed and after freezing, the subsequent polymer thread or lane is dispensed directly on top by offsetting in the z direction. SEM micrographs of the scaffold fabricated by this design at (a) −45° C. and (b) −5° C. are seen in FIGS. 12a and d. The cell-scaffold constructs are kept in static culture in DMEM supplemented with 10% FBS (fetal bovine serum) and 1% AAS (amino acid supplemented medium).

For in vitro studies, 3T3/NIH fibroblasts (CRL-1658, ATCC) are used. Dulbecco's modified Eagle's medium (DMEM) with 4 mM L-glutamine and 4.5 g/l glucose and fetal bovine serum (FBS) are obtained from Hyclone (Logan, Utah, USA). All other reagents are purchased from Sigma-Aldrich Co. and used as received unless otherwise stated. The scaffolds are neutralized in 5% NaOH solution for 30 minutes to remove any possible trace of acetic acid. The scaffolds are then rinsed repeatedly in distilled water. Next, they are immersed in 70 vol. % ethanol overnight for sterilisation. The scaffolds are rinsed 6 times for 15 minutes with 40 ml of phosphate buffered saline (PBS) per rinse and cut into 1.2 cm squares before cell seeding is carried out. The 3T3/NIH fibroblast are cultured following normal culturing conditions well known in the prior art (Sambrook, et al., Molecular Cloning: A Laboratory Manual, Cold Spring Harbour Lab Publ., 1989, Ausubel, et al., Current Protocols in Molecular Biology, Grene Publishing Associates and Wiley-Interscience, 1987 or Schantz, J.-T., Ng, K. W., A Manual for Primary Human Cell Culture, World Scientific Publishing Company, 2004). The fibroblasts are used for seeding onto each scaffold at a density of $4 \times 10^5$ cells/cm$^2$. The cell-scaffold constructs are kept in culture in DMEM supplemented with 10% FBS and 1% antibiotic-antimycotic solution (AAS) for up to 14 days at 37° C. and 5% $CO_2$. The media is changed at Day 3. Scaffolds are removed at Day 3 and Day 6 and are fixed overnight in a automatic tissue processor (Leica TP1020). The constructs are cut into 7 μm sections using a microtome (Leica RM2125RT, Germany) and stained with hematoxylin and eosin for analysis. The staining method involves application of the basic dye hematoxylin, which colors basophilic structures with blue-purple hue, and alcohol-based acidic eosin Y, which colors eosinophilic structures bright pink.

Figure 16:
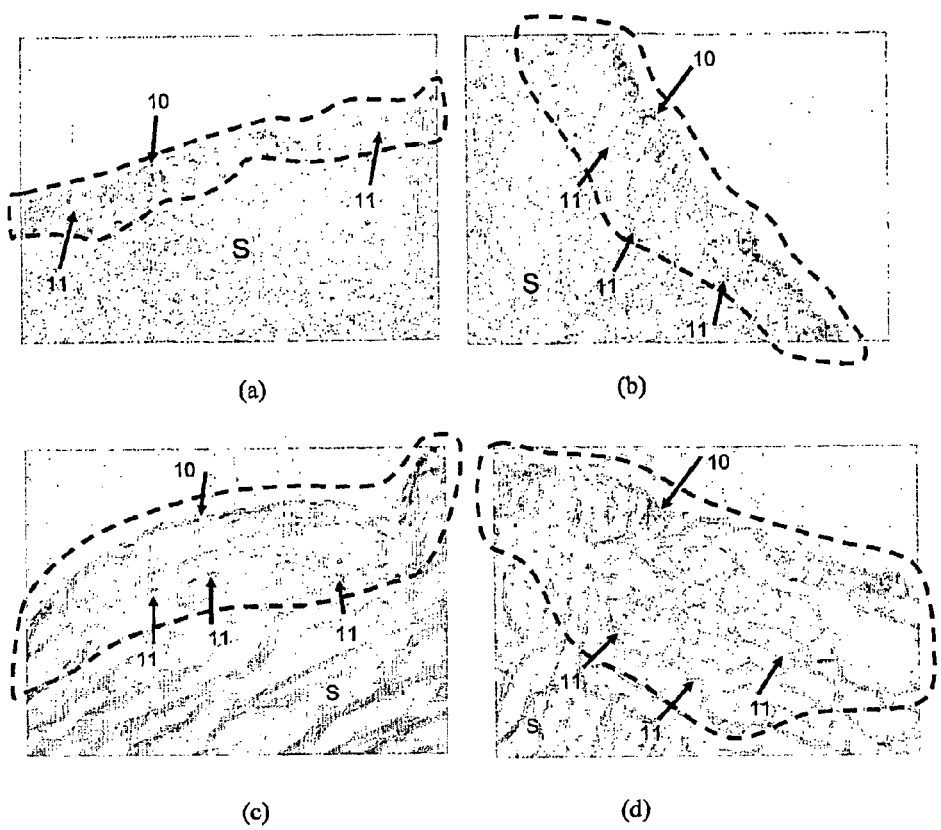
FIG. 16 shows light micrographs of H&E stained slides of chitosan scaffold fabricated at −45° C., (a) at Day 3 after seeding and (b) at Day 6 and chitosan scaffold fabricated at −5° C., (c) at Day 3 after seeding and (d) at Day 6 after seeding. The dotted lines show the area of cell infiltration. S is the scaffold, 10 the cells attached to the scaffold surface, 11 examples of some of the cells which have infiltrated into the scaffold. Cell infiltration can be seen for both scaffolds, however, for the scaffold with larger pore size (micropore size ~90 µm) (FIG. 16 c and d), the cells have infiltrated deeper. It can also be observed that the cells are aligned in the channels of the scaffolds. This data shows that micropore size and orientation of the scaffolds can be used to influence cell infiltration and orientation.

The light microscope (Olympus DP70) pictures taken are shown in FIG. 16. Cell infiltration can be seen for both scaffolds, however, for the scaffold with larger pore size (micropore size about 90 μm) (FIG. 16 c and d), the cells have infiltrated deeper. It can also be observed that the cells are aligned in the channels of the scaffolds. This data shows that micropore size and orientation of the scaffolds can be used to influence cell infiltration and orientation.

Effect of Micropore Sizes and Orientation on Cellular Infiltration and Vascularisation In Vivo The scaffolds used for the in vivo experiment are the same as the one used for the in vitro experiment.

Wistar rats weighing 300 to 350 g are used for the subcutaneous implantation study. Implantation is performed in an aseptic manner under a laminar hood. The rat is anaesthetized with inhalational isoflurane and oxygen, administered via a facemask. A patch of skin on the dorsum is shaved and cleansed with chlorhexidine and iodine. A single 3 cm dorsal midline incision is made. Three subcutaneous pockets are created at the lateral sides of the incision by blunt dissection. The chitosan scaffolds (fabricated at −5° C. (C5; pores size about 90 μm) and −45° C. (C45; pores size about 35 μm)) are inserted into two of the pockets, ensuring that placement is flat and that the scaffolds remained separate from each other. The last pocket is left empty as a negative control for normal healing response. The incision is closed with interrupted 3/0 polypropylene sutures. Postoperatively, an injection of tolfedine 0.1 ml is administered intramuscularly in the thigh for pain relief. Sutures are removed on the tenth post-operative day. At the specified endpoint (4 weeks, 8 weeks post implantation), the rat is euthanized by carbon dioxide inhalation. The dorsum is shaved and the previous incision reopened and extended to visualize all three pockets. Each of the scaffolds and the empty pocket are retrieved with the surrounding tissue. The explants are then fixed overnight in a automatic tissue processor (Leica TP1020) and cut into 7 µm sections using a microtome (Leica RM2125RT, Germany).

Hematoxylin and eosin (H&E) staining and Masson's Trichroming staining are carried out on the sections. Masson's Trichroming staining is suited for distinguishing cells from surrounding connective tissue. It stains keratin and muscle fibers red, collagen and bone blue or green, cytoplasm light red or pink, and cell nuclei dark brown to black.

Figure 17:
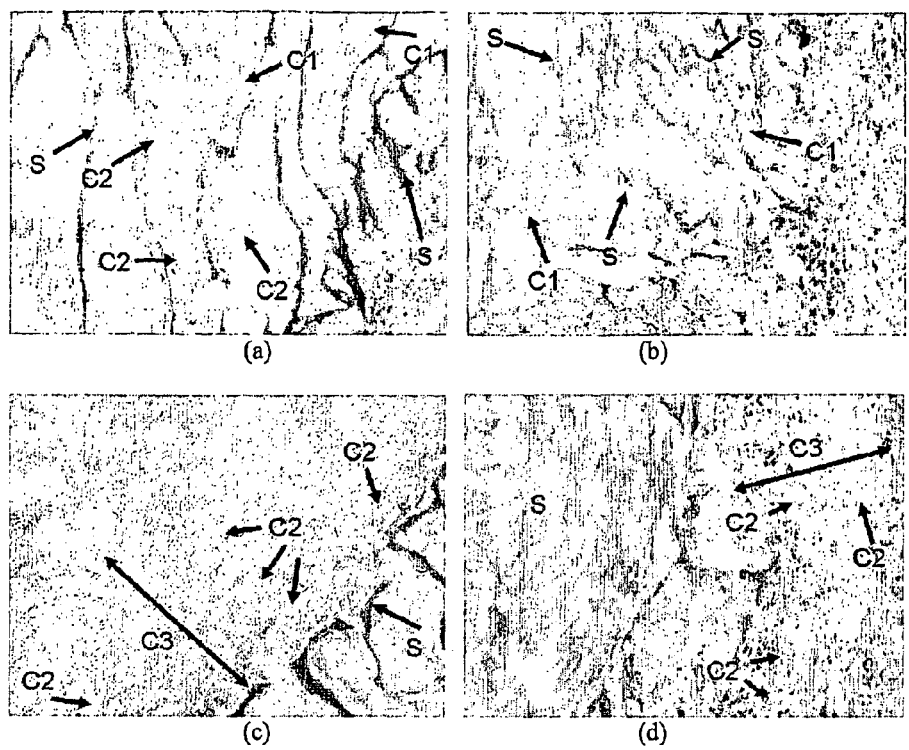
FIG. 17 shows light micrographs of H&E stained slides of explants at 4 weeks, on (a) C5 scaffold which shows cellular infiltration and blood capillaries within, (b) C45 scaffolds showing restriction of cellular infiltration at the scaffold surface, (c) capsule of C5 scaffold which is high vascular and cellular and (d) capsule of C45 scaffold which is highly vascular and cellular. All taken at magnification of ×400. H&E results show that at 4 weeks, cellular infiltration can be observed throughout the C5 scaffolds (FIG. 17a). S indicates the scaffold, C1 indicates cells within the scaffold, C2 indicates blood capillaries within the scaffold and the arrow labeled with C3 shows the thickness of the capsule surrounding the scaffold. Cells can be observed to have infiltrated the whole thickness of the scaffold along the aligned pores of the scaffold S. In addition, neovascularisation can also be observed for the C5 scaffolds. Blood capillaries can be seen infiltrating throughout the scaffold (with red blood cells). However, for the C45 scaffolds (FIG. 17b), cellular infiltration is restricted to about 200 µm from the surface of the scaffold and there were no blood capillaries observed within the scaffold. This can be attributed to the difference in pore sizes of the scaffolds, it can be seen that the larger pore size of 90 µm is much better for cellular infiltration vascularisation of the scaffolds.

H&E results show that at 4 weeks, cellular infiltration can be observed throughout the C5 scaffolds (FIG. 17a). Cells can be observed to have infiltrated the whole thickness of the scaffold along the aligned pores. In addition, neo vascularisation can also be observed for the C5 scaffolds. Blood capillaries can be seen infiltrating throughout the scaffold (with red blood cells). However, for the C45 scaffolds (FIG. 17b), cellular infiltration is restricted to about 200 µm from the surface of the scaffold and there were no blood capillaries observed within the scaffold. This can be attributed to the difference in pore sizes of the scaffolds, it can be seen that the larger pore size of 90 µm is much better for cellular infiltration vascularisation of the scaffolds. This is a very important factor for the tissue engineering scaffolds for functional soft tissues, as blood vessels are required to supply nutrients to the cells within the scaffolds.

Another observation is that the capsules surrounding both scaffolds are relatively thick, ~250 µm. A capsule is formed when a material is implanted into the body. The classic foreign body response invoked will be the formation of an avascular fibrous capsule around the implant, which is similar to scar tissue. The capsules are observed to be highly cellular and vascular, as seen in FIGS. 17c and d.

A fibrous capsule presents a transport barrier in two ways, 1) the diffusion barrier imposed by a densely fibrous capsular tissue or 2) the perfusion barrier imposed by capsular tissue avascularity. However, in the case of the chitosan scaffolds, the capsule is highly cellular, as well as, vascular. Therefore, the capsular tissue should not act as any barrier for transport of nutrients to the cells within the scaffolds. The presence of blood capillaries within the scaffold should further ascertain that.

Figure 18:
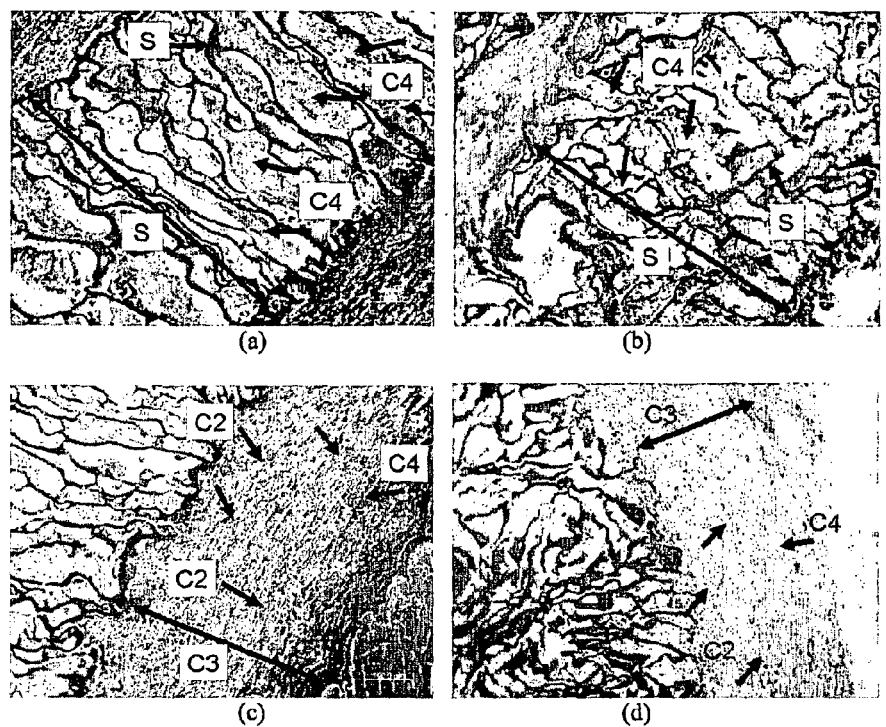
FIG. 18 shows light micrographs of Masson's Trichrome stained slides of explants at 4 weeks, on (a) C5 scaffold which shows collagen deposition within, (b) C45 scaffolds showing some amount of collagen deposits. Collagenous capsule of (c) C5 scaffold (d) C45 scaffold which is also highly vascular and cellular. All were taken at magnification of ×200. S indicates the scaffold, C2 indicates blood capillaries in the capsule, the arrow labeled with C3 shows the thickness of the capsule surrounding the scaffold and C4 indicates collagen deposited in the scaffold and in the capsule surrounding the scaffold. For the C5 scaffold (FIG. 18a), it is observed that collagen is deposited throughout the scaffolds. The micrograph also shows that the collagen is deposited along the aligned pores of the scaffold. As for the C45 scaffold (FIG. 18b), some traces of collagen can be observed within the scaffold but not in such abundance as compared to the C5 scaffold. Higher cellular infiltration for the C5 scaffold results in more neo collagen being deposited. As seen from FIGS. 18(c) and (d), the capsules for both scaffolds show aligned bundles of collagen and are highly cellular.

For the C5 scaffold (FIG. 18a), it is observed that collagen is deposited throughout the scaffolds. The micrograph also shows that the collagen is deposited along the aligned pores of the scaffold. As for the C45 scaffold (FIG. 18b), some traces of collagen can be observed within the scaffold but not in such abundance as compared to the C5 scaffold. Higher cellular infiltration for the C5 scaffold results in more neo collagen being deposited. As seen from FIGS. 18(c) and (d), the capsules for both scaffolds show aligned bundles of collagen and are highly cellular.

Figure 19:
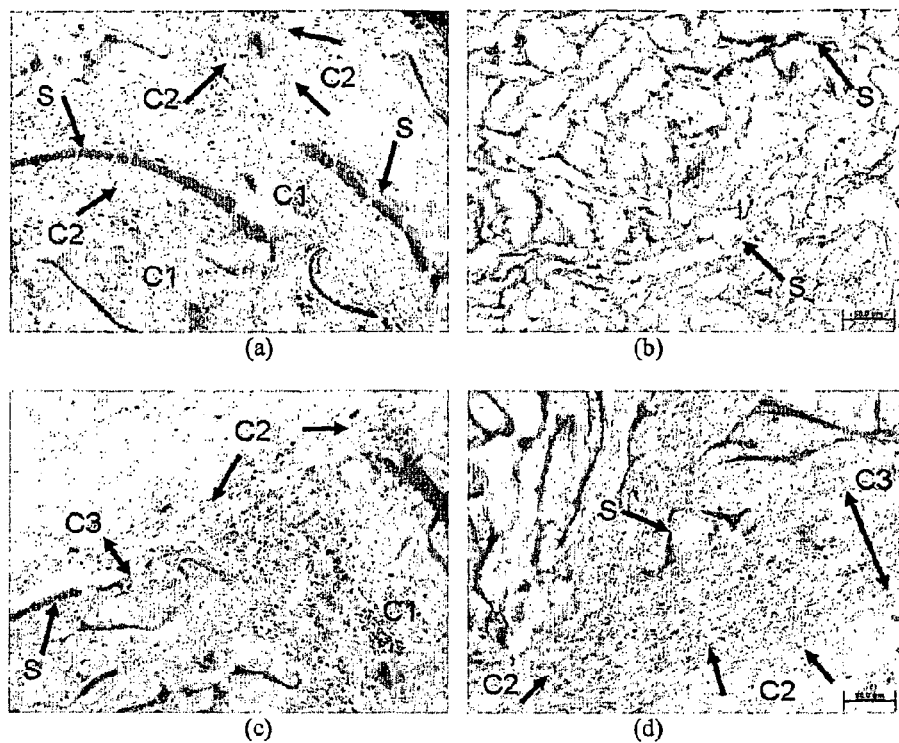
FIG. 19 shows light micrographs of H&E stained slides of explants at 8 weeks, on (a) C5 scaffold which shows cellular infiltration and blood capillaries within, (b) C45 scaffolds showing restriction of cellular infiltration at the scaffold surface, (c) capsule of C5 scaffold which is vascular and cellular and (d) capsule of C45 scaffold which is vascular and cellular. All taken at magnification of ×400. S indicates the scaffold, C1 indicates cells within the scaffold, C2 indicates the position of blood capillaries within the scaffold and in the capsule and the arrow labeled with C3 shows the thickness of the capsule surrounding the scaffold. Cellular infiltration can be observed throughout the scaffold along the aligned pores of the scaffold (FIG. 19a). Blood capillaries can also be observed to have permeated though the scaffold. The capsule of the explant can be observed to be still vascular and cellular and also much thinner (~20 µm) than that explanted at 4 weeks, as seen in FIG. 19(b). C45 scaffolds also show similar cellular infiltration which is restricted to the surface of the scaffold (FIG. 19c). From FIG. 19(d), it is observed that the capsule thickness of the C45 scaffolds (~50 µm) has also decreased.
Figure 20:
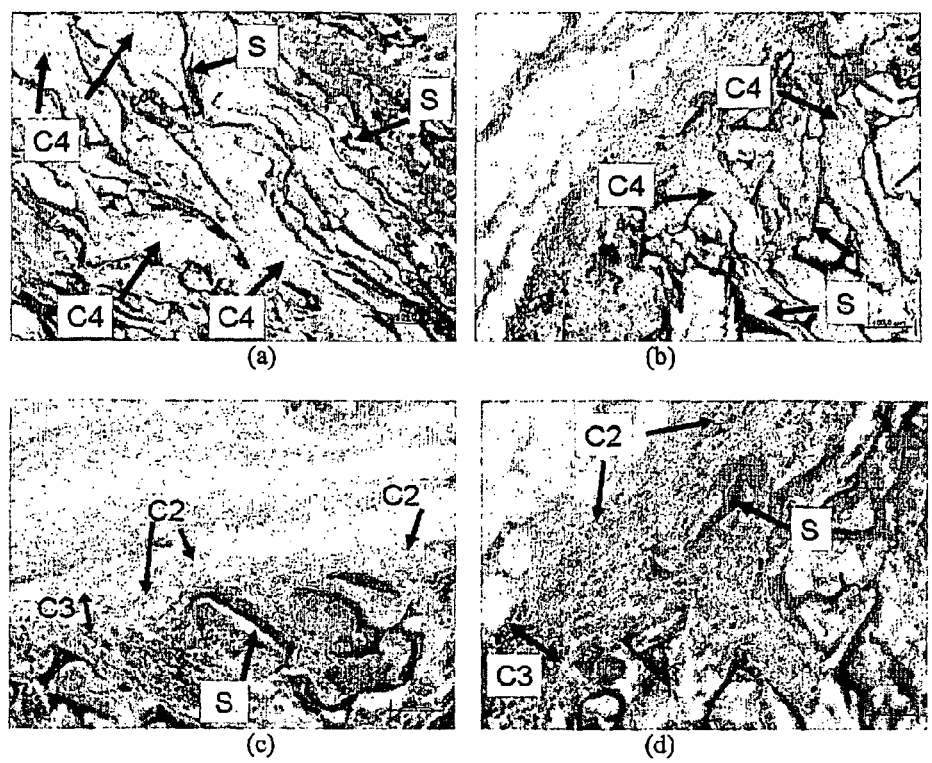
FIG. 20 shows that Masson's Trichrome stains reveal more collagen deposition in C5 scaffolds as compared to C45 at 8 weeks, which is similar to results obtained at 4 weeks.

At 8 weeks, cellular infiltration and vascularisation are observed for C5 scaffolds (FIG. 19a). Cellular infiltration can be observed throughout the scaffold along the aligned pores of the scaffold. Blood capillaries can also be observed to have permeated through the scaffold. The capsule of the explant can be observed to be still vascular and cellular but much thinner (~20 µm) than that explanted at 4 weeks, as seen in FIG. 19(b). The remodelling of the area around the implant which results in the capsule becoming much thinner after 8 weeks, shows that the scaffold can be well integrated when implanted (with no transport barrier). C45 scaffolds also show cellular infiltration which is still restricted to the surface of the scaffold (FIG. 19c). From FIG. 19(d), it is observed that the capsule thickness of the C45 scaffolds (~50 µm) has also decreased. Masson's Trichrome stains reveals more collagen deposition in C5 scaffolds as compared to C45 (FIG. 20) at 8 weeks.

Prior art with in vivo studies carried out with chitosan scaffolds do not show the same degree of cellular infiltration and vascularisation as with the scaffolds in the experiments described above. In a study done with chitosan scaffold (mean pore diameter ~80 µm) fabricated by phase separation, in vivo subcutaneous experiment show that cellular infiltration is limited to 200 µm into the scaffold and vascularisation within the scaffold is not reported (Chupa, J. M., Foster, A. M., et al., 2000, Biomaterials, vol. 21(22), p. 2315-2322).

In another study, subcutaneous experiment was carried out using acellular chitosan-collagen scaffolds and chitosan-collagen scaffolds seeded with preadipocytes (Wu, X. M., Black, L., et al., 2007, Journal of Biomedical Materials Research Part A, vol. 81A(1), p. 59-65). Vascularisation has only been observed for the scaffolds seeded with preadipocytes, the acellular scaffold shows no sign of vascularisation. For cryogenic prototyping scaffolds, vascularisation can be observed for scaffolds which are not seeded with cells.

The invention claimed is:
1. A method of fabricating a three dimensional scaffold suitable for tissue-engineering having a controlled microporous structure and a controlled macroporous structure using cryogenic prototyping comprising:
 a) dispensing a first polymer solution in one direction into a reaction chamber to form a first lane;
   wherein said first polymer solution comprises a first polymer and a first solvent;
   wherein said reaction chamber has a first temperature which is at or below the freezing point of said first solvent;
 b) dispensing a second polymer solution into said reaction chamber to form a second lane;
   wherein said second polymer solution comprises a second polymer and a second solvent;
   wherein said second polymer solution is dispensed such that said second lane is arranged next to said first lane in the same orientation as said first lane and being in contact with said first lane on one side;
   wherein said reaction chamber has a second temperature, wherein said second temperature is the same or different from said first temperature as long as it is at or below the freezing point of said second solvent; and
 c) dispensing further polymer solutions into said reaction chamber by repeating steps a) and b) to form further lanes in a first plane;
 d) repeating steps a) to c) to form further lanes in a next plane,
   wherein at least some of the lanes in said next plane are in contact with said lanes of said first plane;
 e) repeating step d) to form a three-dimensional scaffold comprising different planes of lanes formed by said polymer solutions;
   wherein in any of steps c) to d) said polymer solutions are dispensed such that macropores of said controlled macroporous structure are created;
 f) removing said solvents from said three-dimensional scaffold so obtained, wherein said method further comprises using different time intervals between dispensing of said different planes into said reaction chamber, and further comprises dispensing lanes, threads or drops forming a subsequent plane into said reaction chamber only after the lanes, threads or drops forming the previous plane are frozen.
2. The method according to claim 1, wherein the temperature of said reaction chamber can be varied between about 30° C. to about −196° C.

3. The method according to claim 1, further comprising subsequently dispensing any further lanes, threads or drops for a further plane into said chamber according to the method in claim 1.

4. The method according to claim 1, further comprising decreasing or increasing the pore size of said microporous scaffold structure by increasing and lowering the temperature of said reaction chamber, respectively, as long as the temperature of said reaction chamber is equal or below the freezing point of said solvent or solvents.

5. The method according to claim 1, wherein all polymer solutions used for the fabrication of a three-dimensional scaffold are identical.

6. The method according to claim 1, wherein the bottom of said reaction chamber is made of metal, ceramics, plastics or glass.

7. The method according to claim 1, further comprising using at least one needle for dispensing said polymer solution having varying diameters for the outlet opening of said at least one needle.

8. The method according to claim 7, wherein the diameter of said outlet opening of said at least one needle is in a range of about 0.1 mm to about 2 mm.

9. The method according to claim 7, further comprising varying the speed with which the at least one needle for dispensing said polymer solution into said reaction chamber is moved above said reaction chamber.

10. The method according to claim 1, further comprising changing the pressure with which said polymer solution is dispensed into said reaction chamber.

11. The method according to claim 1, wherein said solvent is organic or inorganic.

12. The method according to claim 1, wherein said solvent is selected from the group consisting of 1,1,1,3,3,3-hexafluoroisopropanol (HFIP), acetone, molten phenol, naphthalene, N,N-dimethylformamide (DMF), water, formic acid, acetic acid, lactic acid, ethanol, trifluoroethanol, xylene, diethylformamide, hexa-fluoro-2-propanol, dioxane, chloroform, dimethylacetamide, dichloromethane, tetrahydrofuran (THF), trifluoroacetic acid, N,N-dimethyl acetamide (DMAc), isopropyl alcohol (IPA), methylene chloride, methyl ethyl ketone, octane, propyl alcohol, pyridine, tetraline, toluene, heptane, hexane, methanol, ethyl ether, ethyl alcohol, ethyl acetate, dichloroethyl, carbon tetrachloride, cresol, chlorobenzene, cyclohexane, n-butyl alcohol, butyl acetate, benzyl alcohol, benzene, sulphuric acid or hexafluoro isopropanol, HFIP and mixtures thereof.

13. The method according to claim 1, wherein said polymer is a biocompatible and/or biodegradable polymer.

14. The method according to claim 1, wherein said polymer is selected from the group consisting of α-tricalcium phosphate, βtricalcium phosphate, poly(D,L-lactide)(PLA), poly(urethanes), poly(siloxanes), poly(silicones), poly(ethylene), poly(vinyl pyrrolidone), poly(2-hydroxy ethyl methacrylate), poly(N-vinyl pyrrolidone), poly(methyl methacrylate), poly(vinyl alcohol)(PVA), poly(acrylic acid), poly(vinyl acetate), polyacrylamide, poly(ethylene-co-vinyl acetate), poly(ethylene glycol), poly(methacrylic acid), polyglycolic acids (PGA), poly(lactide-co-glycolides) (PLGA), nylons, polyamides, polyanhydrides, poly(ethylene-co-vinyl alcohol) (EVOH), polycaprolactone, poly(vinyl acetate), polyvinylhydroxide, poly(ethylene oxide) (PEO), polyorthoesters and copolymers or physical blends of these materials.

15. The method according to claim 1, wherein said polymer is selected from the group consisting of chitosan, collagen, cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, and copolymers or physical blends of these materials.

16. The method according to claim 1, wherein said polymer solution dispensed into said reaction chamber is supplemented with at least one bioactive substance.

17. The method according to claim 1, wherein said removing of said solvent is carried out by a method selected from the group consisting of freeze-drying, sublimation, liquid exchange, and critical point drying (CPD).

* * * * *

UNITED STATES PATENT AND TRADEMARK OFFICE
CERTIFICATE OF CORRECTION

PATENT NO. : 8,557,163 B2  
APPLICATION NO. : 12/517941  
DATED : October 15, 2013  
INVENTOR(S) : Chian et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 524 days.

Signed and Sealed this

Fifteenth Day of September, 2015

Michelle K. Lee
*Director of the United States Patent and Trademark Office*